US010370315B2

(12) United States Patent
Feghali et al.

(10) Patent No.: US 10,370,315 B2
(45) Date of Patent: *Aug. 6, 2019

(54) METHOD OF DEPOLYMERIZING LIGNIN

(71) Applicant: Commissariat A L'energie Atomique Et Aux Energies Alternatives, Paris (FR)

(72) Inventors: Elias Feghali, Montrouge (FR); Thibault Cantat, Issy les Moulineaux (FR)

(73) Assignee: Commissariat a L'Energie Atomique et aux Energies Alternatives, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/322,866

(22) PCT Filed: Jun. 17, 2015

(86) PCT No.: PCT/IB2015/054567
§ 371 (c)(1),
(2) Date: Jan. 9, 2017

(87) PCT Pub. No.: WO2016/005836
PCT Pub. Date: Jan. 14, 2016

(65) Prior Publication Data
US 2017/0152199 A1 Jun. 1, 2017

(30) Foreign Application Priority Data
Jul. 9, 2014 (FR) ...................................... 14 56637

(51) Int. Cl.
| C08H 7/00 | (2011.01) |
| C05F 11/00 | (2006.01) |
| C07C 37/54 | (2006.01) |
| C07C 39/08 | (2006.01) |
| C07C 39/11 | (2006.01) |
| C07C 41/18 | (2006.01) |
| C07C 37/055 | (2006.01) |

(52) U.S. Cl.
CPC .............. *C07C 37/54* (2013.01); *C05F 11/00* (2013.01); *C07C 37/055* (2013.01); *C07C 41/18* (2013.01); *C08H 6/00* (2013.01); *Y02E 50/343* (2013.01); *Y02W 30/47* (2015.05)

(58) Field of Classification Search
CPC ................................ C07C 37/54; C07C 41/18
See application file for complete search history.

(56) References Cited

U.S. PATENT DOCUMENTS

| 4,647,704 | A | * | 3/1987 | Engel | ...................... | C07C 37/52 |
| | | | | | | 568/716 |
| 6,214,976 | B1 | * | 4/2001 | Watanabe | ................ | C08H 6/00 |
| | | | | | | 530/500 |
| 8,378,020 | B1 | * | 2/2013 | Balakshin | ................ | C08H 6/00 |
| | | | | | | 524/700 |
| 9,382,225 | B2 | * | 7/2016 | Samec | ...................... | C07C 1/22 |
| 9,765,044 | B2 | * | 9/2017 | Socha | .................. | C07D 307/52 |
| 2012/0108798 | A1 | * | 5/2012 | Wenger | ...................... | C12P 7/10 |
| | | | | | | 530/500 |
| 2013/0060071 | A1 | * | 3/2013 | Delledonne | ............. | C07C 37/54 |
| | | | | | | 585/310 |
| 2013/0231295 | A1 | * | 9/2013 | Gu | ........................... | C07G 1/00 |
| | | | | | | 514/22 |
| 2014/0011248 | A1 | * | 1/2014 | Medoff | ................ | C07D 307/68 |
| | | | | | | 435/136 |
| 2014/0051872 | A1 | * | 2/2014 | Blank | .................. | C07D 309/02 |
| | | | | | | 549/415 |
| 2014/0091256 | A1 | * | 4/2014 | Grubbs | ................. | C07C 321/26 |
| | | | | | | 252/183.13 |
| 2014/0096830 | A1 | * | 4/2014 | Gastaldo | ................. | C07C 41/01 |
| | | | | | | 137/1 |
| 2014/0135470 | A1 | * | 5/2014 | Murray | ................ | C08G 63/183 |
| | | | | | | 528/308.3 |
| 2015/0337214 | A1 | * | 11/2015 | Murray | .................... | C10G 3/45 |
| | | | | | | 585/357 |
| 2016/0024545 | A1 | * | 1/2016 | Dadi | ....................... | C07C 27/00 |
| | | | | | | 435/99 |
| 2016/0130202 | A1 | * | 5/2016 | Barta | ...................... | C07C 51/09 |
| | | | | | | 530/507 |
| 2017/0137446 | A1 | * | 5/2017 | Feghali | ................. | C07F 7/1852 |

FOREIGN PATENT DOCUMENTS

WO    WO 2011/003029 A2    1/2011

OTHER PUBLICATIONS

Gevorgyan et al. J. Org. Chem. 2000, 65, 6179-6186 (Year: 2000).*
Yang et al. Journal of the American Chemical Society, 2008, 130, 17509-17518 (Year: 2008).*
International Search Report and Written Opinion from corresponding International Patent Application No. PCT/IB2015/054567 dated Sep. 21, 2015.
Jianfeng Zhang et al.; "Reductive Degradation of Lignin and Model Compounds by Hydrosilanes"; ACS Sustainable Chemistry & Engineering; vol. 2, No. 8; Jul. 3, 2014; pp. 1983-1991; XP055171789.
Elias Feghali et al.; "Unprecedented Organocatalytic Reduction of Lignin Model Compounds to Phenols and Primary Alcohols Using Hydrosilanes"; Chemical Communications; vol. 50, No. 7; Jan. 1, 2014; pp. 862-865; XP055171824.

* cited by examiner

Primary Examiner — Liam J Heincer
(74) Attorney, Agent, or Firm — Alston & Bird LLP

(57) ABSTRACT

A method of depolymerizing lignin and to the use of this method in the production of fuels, electronic components, plastic polymers, rubber, medicines, vitamins, cosmetic products, perfumes, foodstuffs, synthetic threads and fibers, synthetic leathers, adhesives, pesticides and fertilizers is provided. It also relates to a method of producing fuels, electronic components, plastic polymers, rubber, medicines, vitamins, cosmetic products, perfumes, foodstuffs, synthetic threads and fibers, synthetic leathers, adhesives, pesticides and fertilizers, including a step of depolymerizing lignin using the method according to the invention.

13 Claims, 5 Drawing Sheets

| Bond | Softwood (spruce) % | Hardwood (birch) % |
|---|---|---|
| β-O-4 | 46 | 60 |
| α-O-4 | 6-8 | 6-8 |
| 4-O-5 | 3.5-4 | 6.5 |
| β-5 | 9-12 | 6 |
| 5-5 | 9.5-11 | 4.5 |
| β-1 | 7 | 7 |
| β-β | 2 | 3 |
| Others | 13 | 5 |

1-silacyclo-3-pentene    1-methyl-1-hydrido-2,3,4,5-tetraphenyl-1-silacyclopentadiene methyl siloxane 1-phenyl-1-silacyclohexane 1-sila-bicyclo[2.2.1]heptane 1-methyl-1-silacyclopentane    9,9-dihydro-5-silafluorene

METHOD OF DEPOLYMERIZING LIGNIN

FIELD

The present invention relates to a method of depolymerizing lignin and the use of this method in the manufacture of fuels, electronic components, plastics, rubber, medicinal products, vitamins, cosmetics, perfumes, food products, synthetic yarn and fibers, synthetic leather, adhesives, pesticides, and fertilizers.

It also relates to a method of manufacturing fuels, electronic components, plastics, rubber, medicinal products, vitamins, cosmetics, perfumes, food products, synthetic yarn and fibers, synthetic leather, adhesives, pesticides, and fertilizers, comprising a step of depolymerizing lignin by the method according to the invention.

BACKGROUND

Wood consists of three major constituents: cellulose, hemicellulose and lignin. Cellulose and hemicellulose are already utilized in industry, in particular in the papermaking industry. Each year this use generates several million tonnes of lignin-rich byproducts, which are used as fuels of low calorific value for supplying heat and energy for the papermaking processes. In parallel, a minimal amount of lignin is isolated by direct extraction from plants (F. G. Calvo-Flores and J. A. Dobado, *ChemSusChem.* 2010, 3, pages 1227-1235).

Lignin is the most abundant substance in nature in terms of a source of aromatic groups and the greatest contributor of organic matter to the soil (S. Y. Lin, in Methods in Lignin Chemistry, Springer Series in Wood Science (Ed.: C. W. Dence), Springer, Berlin 1992). It results from the radical polymerization of three monomers called monolignols: p-coumaryl alcohol, coniferyl alcohol, and sinapyl alcohol, which after polymerization by dehydrogenation with peroxidase give the p-hydroxyphenyl (H), guaiacyl (G), and syringyl (S) residues respectively, as illustrated in FIG. 1 (R. Vanholme, K. Morreel, J. R. W. Boerjan, *Curr. Opin. Plant Biol.* 2008, 11, pages 278-285).

The complexity and the diversity of the structure of lignin largely depend on its origin. Taking plant taxonomy as a basis, it has been proposed that lignin from gymnosperms (called softwood, or "bois tendre" in French) has more G residues, than that from the angiosperms (called hardwood, or "bois dur" in French), which contains a mixture of residues G and S, and the lignin from herbaceous plants contains a mixture of the three aromatic residues H, G and S. A more rigorous classification technique was to adopt a chemical approach as a basis, in which the lignins are classified according to the abundance of the units G, H and S in the polymer. Four main groups of lignin have thus been identified: type G, type GS, type HGS and type HG (F. G. Calvo-Flores and J. A. Dobado, *ChemSusChem.* 2010, 3, pages 1227-1235).

Regardless of the type of lignin, this biopolymer is characterized by considerable chemical heterogeneity and consists of propyl-phenol units joined together by various types of C—O and C—C bonds of the aryl ether, aryl glycerol and β-aryl ether type. FIG. 2 shows the structure of lignin proposed by E. Adler, *Wood Sci. Technol.* 1977, 11, page 169.

Ether bonds represent about two thirds of the bonds. More specifically, the bonds of the β-O-4 and α-O-4 type, which form part of the alkaryl ethers, are the most abundant. Typically, lignin from angiosperms (hardwood, or bois dur in French) contains 60% of bonds of the β-O-4 type and 6-8% of the α-O-4 type, and lignin from gymnosperms (softwood or bois tendre in French) contains 46% of bonds of the β-O-4 type and 6-8% of the α-O-4 type. Although the proportion of these bonds varies considerably from one species to another, typical values taken from M. P. Pandey, C. S. Kim, *Chem. Eng. Technol.,* 2011, 34, 29, are listed in the table in FIG. 3.

The chemical structures of the most abundant types of bonds in lignin are shown in FIG. 4.

Lignin represents the largest renewable reservoir of available aromatic compounds. Owing to its high aromatics content, lignin has great potential for functioning as an alternative to the nonrenewable fossil resources for producing aromatic chemicals with high added value, i.e. products whose transformation increases their commercial value considerably. As aromatic chemicals with high added value, we may mention, for example, 4-propylbenzene-1,2-diol (at 3700 $/kg) or 4-(3-hydroxypropyl)-1,2-benzenediol (at 3100 $/kg). Thus, upgrading of lignin involves its conversion to valuable, useful aromatic products via its depolymerization. However, owing to its amorphous, polymeric structure based on strong ether bonds, its depolymerization to produce usable molecules presents a challenge. Moreover, lignins are very varied structurally and, depending on the plant source used, they contain different proportions of the three basic monomers (p-coumaryl alcohol, coniferyl alcohol and sinapyl alcohol).

Development of a method of depolymerization by cleavage of the ether bonds will therefore contribute significantly to the upgrading of lignin. Now, direct depolymerization of lignin is difficult, as its structure is highly functionalized and branched and its steric hindrance may limit access of the catalyst to the active sites. Moreover, the chemical heterogeneity of lignin, which is due to the presence of several residues G, H, S present at variable levels depending on the nature of the plant, and to the presence of various types of C—O and C—C bonds of the aryl ether, aryl glycerol and β-aryl ether type, complicates the production of pure chemicals during transformation of lignin.

In view of the difficulty of carrying out direct depolymerization of lignin, scientists have synthesized chemically pure models that are representative of the ether bonds present in lignin, for studying the reactivity (J. Zakzeski, P. C. A. Bruijnincx, A. L. Jongerius and B. M. Weckhuysen, *Chem Rev.,* 2010, 110, page 3552). Most studies aiming at depolymerization of lignin have focused on these models and have not considered the complex structure of natural lignins. Examples of cleavage of C—O bonds of the β-O-4 unit on models of lignin using redox or reductive catalysis are given hereunder.

Bergman, Ellman et al. (J. M. Nichols, L. M. Bishop, R. G. Bergman, J. A. Ellman, *J. Am. Chem. Soc.* 2010, 132, pages 12554-12555) have developed a reaction of ruthenium-catalyzed redox cleavage of the C—O bond. The models of the β-O-4 units of lignin were cleaved with yields isolated ranging from 62 to 98%. The reaction takes place according to a tandem mechanism of dehydrogenation of the α-alcohol followed by reductive cleavage of the aryl ether.

In addition, James et al. (A. Wu, B. O. Patrick, E. Chung and B. R. James, *Dalton Trans.,* 2012, 41, page 11093) have shown that a ruthenium complex is able to catalyze the direct hydrogenolysis of the ketone equivalent of the β-O-4 unit with gaseous hydrogen. However, the authors observed that models of the β-O-4 unit containing the γ-OH function were not reactive.

Recently, Leitner et al. (T. vom Stein, T. Weigand, C. Merkens, Jurgen Klankermayer, W. Leitner, *ChemCatChem*, 2013, 5, pages 439-441) described a reaction of redox cleavage of C—O bonds of the β-O-4 unit, by intramolecular hydrogen transfer. This reaction employs a catalyst based on ruthenium (an expensive noble metal), a triphos ligand (a ligand that is also very expensive) and high temperatures (heating at 135° C.). Moreover, depending on the model of the β-O-4 unit used, the reaction may prove more or less simple to carry out.

A vanadium catalyst was used by Toste et al. (S. Son and F. D. Toste, *Angew. Chem. Int. Ed.* 2010, 49, pages 3791-3794) for cleavage of C—O bonds of the β-O-4 unit and formation of aryl enones. This redox transformation is carried out in ethyl acetate at 80° C. The catalyst charge is 10 mol %, and after 24 hours the reaction may reach 95% conversion of the starting lignin model to aryl enone. As it is a redox reaction, the products obtained are generally highly oxygenated and therefore poor in energy.

More recently, the same group (J. M. W. Chan, S. Bauer, H. Sorek, S. Sreekumar, K. Wang, F. D. Toste, *ACS Catal.*, 2013, 3, pages 1369-1377) demonstrated the applicability of this method of redox cleavage to the degradation of lignin extracted from *Miscanthus giganteus* (elephant grass). The results of GC and 2D NMR studies of the degradation of dioxasolv and acetosolv lignin were similar to the data obtained with the lignin models, which confirms the selectivity of the method for the β-O-4 bonds. Moreover, only *Miscanthus giganteus*, which is a grass, was tested, not wood. Finally, using GC/MS, the authors were able to identify and quantify volatile phenolic compounds (such as vanillin, vanillic acid, syringic acid and syringaldehyde) produced in the reaction. However, no pure chemical could be isolated by this method, and partially characterized mixtures were obtained.

In 2011, a selective method of hydrogenolysis of the aromatic C—O bonds in alkaryl ethers and diaryl ethers was developed by Sergeev and Hartwig (A. G. Sergeev and J. F. Hartwig, *Science*, 2011, 332, page 439). This method allows selective formation of arenes and alcohols starting from lignin models and using a soluble nickel-carbene complex. The reaction is carried out in m-xylene, under 1 bar of hydrogen and at temperatures ranging from 80 to 120° C. Use of this method allows cleavage of models of the 4-O-5 bond (diaryl ether), to give anisole, benzene, and phenols at moderate yields. Moreover, hydrogenolysis of models of the α-O-4 unit of lignin at 80° C. under 1 bar of hydrogen gives 3,4-dimethoxytoluene and 2-methoxyphenol at almost quantitative yields. Cleavage of the β-O-4 model in basic conditions is carried out without the presence of catalyst and supplies guaiacol at 89% yield but mixed with many other products.

The Toste, Ellman and Hartwig groups have combined their results on the reduction of lignin and of its models in homogeneous catalysis in international application WO2011003029. The precursors used are derivatives of vanadium, ruthenium and rhodium. Only the complexes based on vanadium and ruthenium were used for redox depolymerization of lignin extracted from *Miscanthus giganteus*. However, it was not possible to isolate or identify a pure chemical by this method, and partially characterized mixtures were obtained.

In 2009, Ragauskas et al. (M. Nagy, K. David, G. J. P. Britovsek and A. J. Ragauskas, *Holzforschung*, 2009, 63, page 513) succeeded in depolymerizing ethanol organosolv lignin (EOL) (ethanol-soluble) from pine in reducing conditions. In this study, classical heterogeneous catalysts as well as new homogeneous catalysts were used for cleaving diaryl ether and dialkyl ether bonds. Using the hydrogenolysis conditions: 5 MPa $H_2$; 175° C.; 20 hours, the ruthenium catalyst is effective in increasing the solubility of lignin (solubility up to 96%) and contributes to its degradation. A decrease of the order of 10% to 20% in the weight-average molecular weight (Mw) was obtained (Mw=1900-2100 g/mol), which corresponds to a degree of polymerization (DP) of 10 to 11 monomer units (L. B. Davin, N. G. Lewis, *Curr. Opin. Biotechnol.*, 2005, 16, pages 407-415). Moreover, according to the authors, hydrogenolysis of the diaryl ether and alkaryl ether groups is accompanied by a simultaneous hydrogenation reaction of the aromatic ring. Finally, identification as well as the detailed formation of the reaction products and cleavage pathways were not elucidated.

In 2013, the organocatalytic reduction of lignin model compounds was first described by Feghali and Cantat (E. Feghali, T. Cantat, *Chem. Commun.*, 2014, 50, pages 862-865). They showed that $B(C_6F_5)_3$ is an efficient, selective hydrosilylation catalyst for reductive cleavage of alkaryl ether bonds and particularly models of α-O-4 and β-O-4 units. Moreover, reduction takes place in mild conditions (room temperature, from 2 to 16 hours), and may be carried out with a source of hydride that is stable in air and inexpensive, such as polymethylhydrosiloxane (PMHS) and tetramethyldisilazane (TMDS). However, this method could not be extrapolated to the direct depolymerization of lignin.

In view of the complex, heterogeneous and strongly hindered polymeric structure of lignin, which complicates its depolymerization, the methods of depolymerization developed in the literature and described above are generally carried out in harsh conditions of temperature and pressure and employ metals in larger catalytic amounts. Moreover, these methods were developed on chemically pure models, and few could be extrapolated to the reduction of lignin. In fact, only the methods of Ragauskas et al. (M. Nagy, K. David, G. J. P. Britovsek and A. J. Ragauskas, *Holzforschung*, 2009, 63, page 513) and of Toste et al. (S. Son and F. D. Toste, *Angew. Chem. Int. Ed.* 2010, 49, pages 3791-3794) could be extrapolated to lignin. The other methods did not work with lignin. The presence of several impurities, notably water, oxygen ($O_2$), sulfur-containing molecules, phosphorus-containing molecules and sugar residues may deactivate the catalyst. These impurities may, for example, be derived from lignocellulose or from the method of extraction of lignin from lignocellulose.

There is therefore a real need for a method for depolymerizing lignin that overcomes the drawbacks of the prior art.

In particular, there is a real need for a method for depolymerizing lignin, said method:

being very efficient, reflected in a high level of conversion of lignin to smaller molecules containing 1 or 2 aromatic rings, and highly selective for certain bonds in lignin;

allowing aromatic molecules of high added value to be generated, in particular molecules containing 1 or 2 aromatic rings;

being simple to carry out;
and can be carried out in mild, industrially interesting operating conditions.

SUMMARY

The present invention has precisely the aim of responding to these needs, by providing a method of depolymerizing lignin to molecules containing 1 or 2 aromatic rings, by selective cleavage of the sp³ carbon-oxygen bond of alkaryl ethers of the β-O-4, α-O-4, β-5, β-1, β-β type present in lignin, characterized in that
a lignin with a level of sulfur below 1.5 wt %, relative to the total weight of the lignin, is reacted, in the presence of a catalyst, with
a silane compound of formula (I)

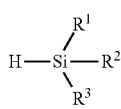

in which
R¹, R² and R³ represent, independently of one another, a hydrogen atom, a halogen atom, a hydroxyl group, an alkyl group, an alkenyl group, an alkynyl group, an alkoxy group, an aryloxy group, a silylated group, a siloxy group, an aryl group, an amino group, said alkyl, alkenyl, alkynyl, alkoxy, silylated, siloxy, aryl and amino groups optionally being substituted, or
R³ is as defined above and R¹ and R², taken together with the silicon atom to which they are bound, form a silylated heterocycle, optionally substituted.

DETAILED DESCRIPTION

Figure 1:
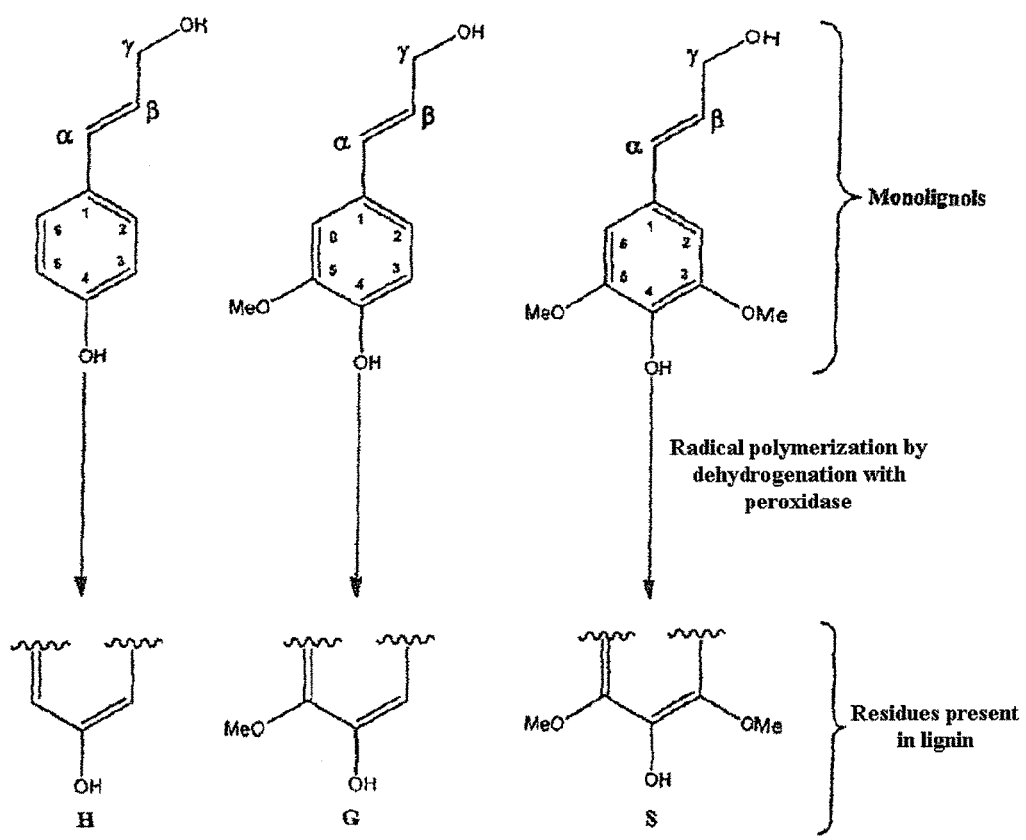
FIG. 1 illustrates the radical polymerization of three monomers to give the p-hydroxyphenyl (H), guaiacyl (G), and syringyl (S) residues present in lignin.
Figures 2, 3:
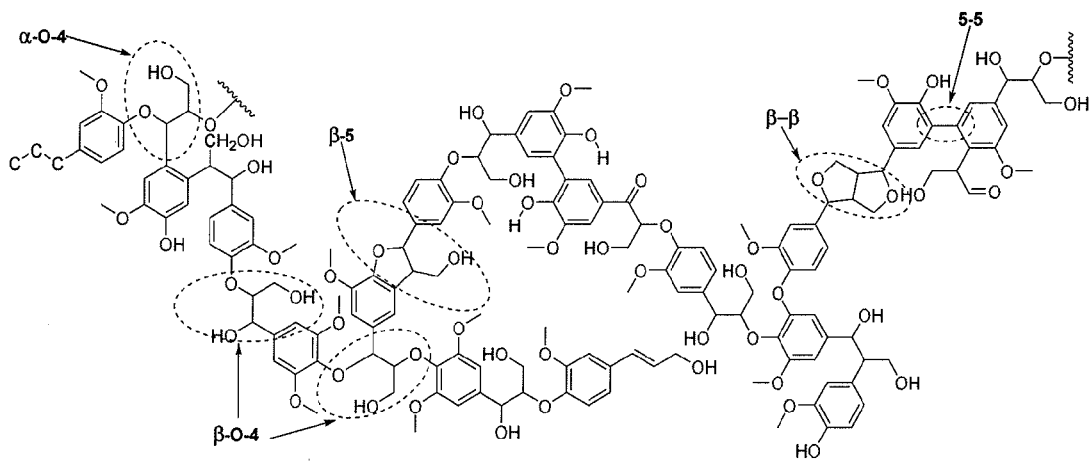
FIG. 2 shows the structure of lignin proposed by E. Adler, *Wood Sci. Technol.* 1977, 11, page 169.
FIG. 3 lists the typical proportions of bonds in species of lignin.
Figure 4:
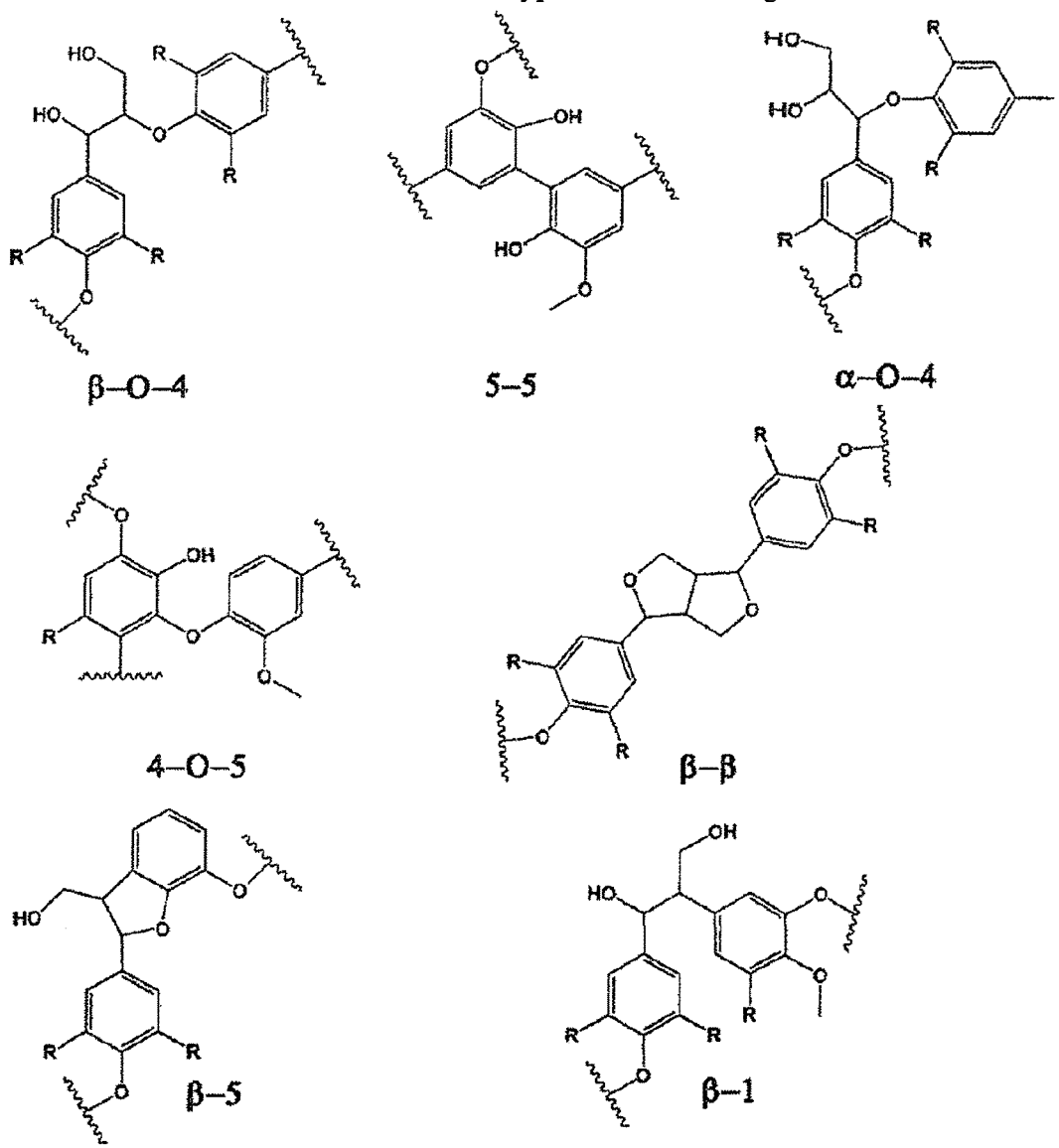
FIG. 4 illustrates the chemical structures of the most abundant types of bonds in lignin.

The method of depolymerizing lignin according to the invention is highly selective with respect to sp³ carbon-oxygen bonds of the alkaryl ethers present in lignin and thus relates essentially to the sp³ carbon-oxygen bonds of the β-O-4, α-O-4, β-5, β-1, and β-β type. Without wishing to be bound by any theory, cleavage of the sp³ carbon-oxygen bonds at the level of the bonds of the β-O-4, α-O-4 and β-β type leads both to depolymerization of lignin and modification of its structure, whereas cleavage of the sp³ carbon-oxygen bonds at the level of the bonds of the β-5 and β-1 type leads to modification of the structure of the lignin without cleavage of the bond between two successive monomer units.

The sp² carbon-oxygen bonds of the aryl ethers present in lignin (essentially the bonds of the 5-5 and 4-O-5 type), as well as any other sp² carbon-oxygen bond present in lignin, remain intact during the method of the invention.

The method of the invention makes it unnecessary to use the harsh reaction conditions of temperature and pressure used conventionally in the literature for the depolymerization of lignin. It also makes it possible to reduce costs by using the silanes of formula (I), which are stable in air and inexpensive.

The method of the invention has the advantage of allowing the depolymerization of lignin leading to the production of molecules containing 1 or 2 aromatic rings with an average molar mass by weight below 1500 g/mol for the molecules in silylated form (molecules in which all the oxygen atoms are in silylated form O—Si) or with an average molar mass by weight less than or equal to 450 g/mol, preferably less than or equal to 400 g/mol for the molecules in nonsilylated form (i.e. molecules in which all the O—Si bonds have been cleaved, for example by hydrolysis), i.e. a degree of polymerization less than 3 monomer units, preferably between 1 and 2 monomer units. The aromatic molecules obtained may contain mono-, di- or tri-oxygenated aromatic rings depending on the abundance of the G, H and S units in the lignin used. The proportions of the G, H and S units depend on the plant species from which the lignin is obtained as well as its method of extraction. The weight-average molecular weight of the molecules obtained and therefore their degree of polymerization may be determined by any method known by a person skilled in the art, notably by size exclusion chromatography (SEC).

Furthermore, the method of the invention can generate methane and hydrogen (of the order of 7 to 15 wt % of the weight of lignin introduced). These two gases may optionally be used as fuel for supplying energy for the method of the invention.

In the method of the invention, the silane compounds of formula (I) provide cleavage by reduction of the sp³ carbon-oxygen bonds of the alkaryl ethers present in lignin, in catalytic conditions.

The aromatic molecules containing 1 or 2 aromatic rings, with an average molar mass by weight below 1500 g/mol for the molecules in silylated form or with an average molar mass by weight less than or equal to 450 g/mol, preferably less than or equal to 400 g/mol for the molecules in nonsilylated form (i.e. a degree of polymerization less than 3 monomer units, preferably between 1 and 2 monomer units) are thus obtained at a good yield (of the order of 20 to 99%, for example), and with very good selectivity with respect to the sp³ carbon-oxygen bonds β-O-4, α-O-4, β-5, β-1 and β-β.

In the context of the present invention, the yield corresponds to the amount of aromatic molecules containing 1 or 2 aromatic rings, with an average molar mass by weight below 1500 g/mol for the molecules in silylated form or with an average molar mass by weight less than or equal to 450 g/mol, preferably less than or equal to 400 g/mol (i.e. a degree of polymerization less than 3 monomer units, preferably between 1 and 2 monomer units) isolated, relative to the amount of lignin introduced initially:

Yield=$m$(aromatic molecules containing 1 or 2 aromatic rings)/$m$(lignin)

m being the weight in grams.

"Alkyl" means, in the sense of the present invention, a linear, branched or cyclic carbon-containing radical, saturated, optionally substituted, comprising 1 to 12 carbon atoms. As saturated, linear or branched alkyl, we may mention for example the methyl, ethyl, propyl, butyl, pentyl, hexyl, octyl, nonyl, decyl, undecyl, dodecanyl radicals and their branched isomers. As cyclic alkyl, we may mention the cyclopropyl, cyclobutyl, cyclopentyl, cyclohexyl, bicyclo[2,1,1]hexyl, bicyclo[2,2,1]heptyl radicals.

"Alkenyl" or "alkynyl" means an unsaturated linear, branched or cyclic carbon-containing radical, optionally substituted, said unsaturated carbon-containing radical comprising 2 to 12 carbon atoms comprising at least one double bond (alkenyl) or triple bond (alkynyl). We may mention, as examples, the ethylenyl, propylenyl, butenyl, pentenyl, hexenyl, acetylenyl, propynyl, butynyl, pentynyl, hexynyl radicals and their branched isomers. As unsaturated cyclic alkenyls, we may mention for example cyclopentenyl, cyclohexenyl.

The alkyl, alkenyl and alkynyl groups, in the sense of the invention, may optionally be substituted with one or more hydroxyl groups; one or more alkoxy groups; one or more halogen atoms selected from the fluorine, chlorine, bromine and iodine atoms; one or more nitro groups (—NO$_2$); one or more nitrile groups (—CN); one or more aryl groups, with the alkoxy and aryl groups as defined in the context of the present invention.

The term "aryl" generally denotes a cyclic aromatic substituent comprising 6 to 20 carbon atoms. In the context of the invention the aryl group may be mono- or polycyclic. As a guide, we may mention the phenyl, benzyl and naphthyl groups. The aryl group may optionally be substituted with one or more hydroxyl groups, one or more alkoxy groups, one or more "siloxy" groups, one or more halogen atoms selected from the fluorine, chlorine, bromine and iodine atoms, one or more nitro groups (—NO$_2$), one or more nitrile groups (—CN), one or more alkyl groups, with the alkoxy and alkyl groups as defined in the context of the present invention.

The term "heteroaryl" generally denotes a mono- or polycyclic aromatic substituent comprising 5 to 10 ring members, including at least 2 carbon atoms, and at least one heteroatom selected from nitrogen, oxygen, boron, silicon, phosphorus and sulfur. The heteroaryl group may be mono- or polycyclic. As a guide, we may mention the furyl, benzofuranyl, pyrrolyl, indolyl, isoindolyl, azaindolyl, thiophenyl, benzothiophenyl, pyridyl, quinolinyl, isoquinolyl, imidazolyl, benzimidazolyl, pyrazolyl, oxazolyl, isoxazolyl, benzoxazolyl, thiazolyl, benzothiazolyl, isothiazolyl, pyridazinyl, pyrimidilyl, pyrazinyl, triazinyl, cinnolinyl, phthalazinyl, and quinazolinyl groups. The heteroaryl group may optionally be substituted with one or more hydroxyl groups, one or more alkoxy groups, one or more halogen atoms selected from the fluorine, chlorine, bromine and iodine atoms, one or more nitro groups (—NO$_2$), one or more nitrile groups (—CN), one or more aryl groups, one or more alkyl groups, with the alkyl, alkoxy and aryl groups as defined in the context of the present invention.

The term "alkoxy" signifies an alkyl, alkenyl and alkynyl group, as defined above, bound by an oxygen atom (—O-alkyl, O-alkenyl, O-alkynyl).

The term "aryloxy" signifies an aryl group as defined above, bound by an oxygen atom (—O-aryl).

The term "heterocycle" generally denotes a mono- or polycyclic substituent, comprising 5 to 10 ring members, saturated or unsaturated, containing from 1 to 4 heteroatoms selected independently of one another from nitrogen, oxygen, boron, silicon, phosphorus and sulfur. As a guide, we may mention the morpholinyl, piperidinyl, piperazinyl, pyrrolidinyl, imidazolidinyl, imidazolinyl, pyrazolidinyl, tetrahydrofuranyl, tetrahydropyranyl, thianyl, oxazolidinyl, isoxazolidinyl, thiazolidinyl, isothiazolidinyl substituents. The heterocycle may optionally be substituted with one or more hydroxyl groups, one or more alkoxy groups, one or more aryl groups, one or more halogen atoms selected from the fluorine, chlorine, bromine and iodine atoms, one or more nitro groups (—NO$_2$), one or more nitrile groups (—CN), one or more alkyl groups, with the alkyl, alkoxy and aryl groups as defined in the context of the present invention.

Halogen atom means an atom selected from the fluorine, chlorine, bromine and iodine atoms.

"Silylated" group means a group of formula [—Si(X)$_3$] in which each X, independently of one another, is selected from a hydrogen atom; one or more halogen atoms selected from the fluorine, chlorine, bromine or iodine atoms; one or more alkyl groups; one or more alkoxy groups; one or more aryl groups; one or more siloxy groups; with the alkyl, alkoxy, aryl and siloxy groups as defined in the context of the present invention. When at least one of the X represents several siloxy groups, said siloxy groups may be repeated several times so as to lead to polymeric organosilanes of general formula

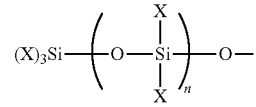

in which X is as defined above and n is an integer between 1 and 20000, advantageously between 1 and 5000, more advantageously between 1 and 1000. Examples that may be mentioned are polydimethylsiloxane (PDMS), polymethylhydroxysiloxane (PMHS) and tetramethyldisiloxane (TMDS).

"Siloxy" group means a silylated group, as defined above, bound by an oxygen atom (—O—Si(X)$_3$) with X as defined above.

Figure 5:
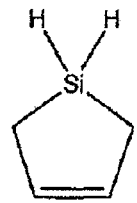
FIG. 5 illustrates exemplary silylated heterocycles according to embodiments of the present disclosure.
Figure 5:
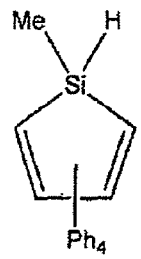

In the sense of the invention, "silylated heterocycle" means a mono- or polycyclic substituent, comprising 5 to 15 ring members, saturated or unsaturated, containing at least one silicon atom and optionally at least one other heteroatom selected from nitrogen, oxygen and sulfur. Said silylated heterocycle may optionally be substituted with one or more hydroxyl groups; one or more alkyl groups, one or more alkoxy groups; one or more halogen atoms selected from the fluorine, chlorine, bromine and iodine atoms; one or more aryl groups, with the alkyl, alkoxy and aryl groups as defined in the context of the present invention. Among the silylated heterocycles, we may mention for example, 1-silacyclo-3-pentene or 1-methyl-1,1-dihydrido-2,3,4,5-tetraphenyl-1-silacyclopentadiene, according to the formulas in FIG. 5.

Figure 6:
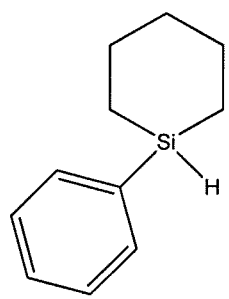
FIG. 6 illustrates exemplary silylated heterocycles according to embodiments of the present disclosure.
Figure 6:
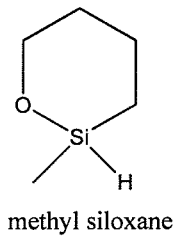
Figure 6:
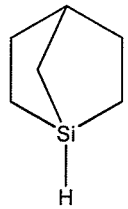
Figure 6:
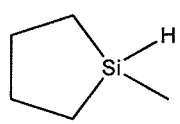
Figure 6:
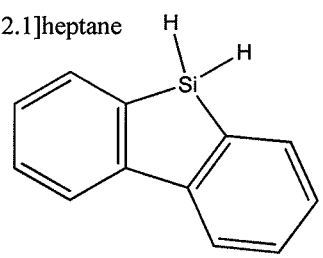

We may also mention, for example, methylsiloxane, 1-phenyl-1-silacyclohexane, 1-sila-bicyclo[2.2.1]heptane, 1-methyl-1-silacyclopentane, 9,9-dihydro-5-silafluorene corresponding to the formulas in FIG. 6.

Polyol means: an organic compound characterized by the presence of a certain number of hydroxyl groups (—OH). In the context of this invention, a polyol compound contains at least one hydroxyl group. In this context, polyol means a compound of formula Z—(OH)$_n$, in which n is greater than or equal to 1, and Z is selected from one or more alkyl groups, one or more alkoxy groups, one or more siloxy groups, one or more aryl groups, one or more heteroaryl groups, with the alkyl, alkoxy and aryl groups as defined in the context of the present invention.

"Amino" group means a group of formula —NR$^4$R$^5$, in which:

$R^4$ and $R^5$ represent, independently of one another, a hydrogen atom, an alkyl group, an alkenyl group, an alkynyl group, an aryl group, a heteroaryl group, a heterocycle, a silylated group, a siloxy group, with the alkyl, alkenyl, alkynyl, aryl, heteroaryl, heterocycle, silylated, and siloxy groups as defined in the context of the present invention; or $R^4$ and $R^5$, taken together with the nitrogen atom to which they are bound, form a heterocycle optionally substituted with one or more hydroxyl groups; one or more alkyl groups; one or more alkoxy groups; one or more halogen atoms selected from the fluorine, chlorine, bromine and iodine atoms; one or more nitro groups (—NO$_2$); one or more nitrile groups (—CN); one or more aryl groups; with the alkyl, alkoxy and aryl groups as defined in the context of the present invention.

"Wood" means a plant tissue that corresponds to the secondary xylem in plants. The term wood includes all the secondary tissues forming the stems, branches and roots of woody plants.

"Lignin" means a biopolymer present in all plants and mainly in vascular plants, woody plants, herbaceous plants and algae. Lignin is one of the principal components of wood. Lignin is a polyol rich in aryl groups as defined above. It is obtained from a plant tissue, notably leaves, herbaceous stems and woody stems. Depending on its method of extraction and its origin, lignin may contain other chemical groups, for example alkenes, alkynes, primary, secondary and tertiary alcohols, ketones, carboxylic acids, acetals, hemiacetals, enols, ethers, esters, allylic alcohols, homoallylic alcohols, nitriles, imines, primary, secondary and tertiary amines, amides, halogens, sulfides, thiols, sulfonates, sulfones, sulfates, sulfoxides.

In the method of the invention, the choice of the plant species from which to extract the lignin and its method of extraction have an important effect notably on the nature of the molecule containing 1 or 2 aromatic rings that we wish to obtain and therefore the selectivity of the method of the invention, on the yield of the method of the invention, on the degree of purity of said aromatic compound and on the productivity of the depolymerization step. As the percentage of residue able to give the desired molecule increases in the species, the more the yield of the process increases.

The plant species is selected taking into account the parameters described below.

a) The plant species selected should advantageously contain a relatively high percentage, i.e. at least 10 wt % of lignin relative to the total weight of the sample of the plant species selected, so as to increase the total yield of the final molecule containing 1 or 2 aromatic rings relative to the starting material, for example wood.

b) The plant species must be selected so as to have at least 50% of G, H or S residue relative to the total number of residues present in the lignin used. It should be noted that the percentage of the residues present in lignin can be determined by techniques known by a person skilled in the art, for example pyrolysis, NMR, etc. This parameter plays an important role in selectivity with respect to the molecule containing 1 or 2 aromatic rings that will be obtained as well as in the increase in the yield of said molecule containing 1 or 2 aromatic rings. As already stated, lignin contains the residues p-hydroxyphenyl (H), guaiacyl (G), and syringyl (S). However, the complexity and the structure of lignin largely depend on its origin. Now, based on the classification of lignins, we may identify four types: G, GS, HGS and HG.

Type G may be distinguished from the others since the species containing this type of lignin are exclusively made up of residues of type G. This type of lignin is generally obtained from gymnosperms (softwood) and more precisely from the conifer division (Pinophyta), which numbers 600-650 plant species.

For the other types of residues, the natural species always contain mixtures GS or HG, and the lignins obtained from these species are characterized by the S/G or H/G ratio. However, there are species that may be rich in S or H residue. As an example, we may mention the common eucalyptus (*Eucalyptus globulus*), which has an S/G ratio of 6.

There are also genetically modified plant species so as preferably to have a single residue that is predominant. For example, Mansfield changed a ratio S/G=2 to a ratio S/G=12 for the poplar (J. J. Stewart, T. Akiyama, C. Chapple, J. Ralph, and S. D. Mansfield, *Plant Physiol*. 2009, 150, pages 621-635). It should be noted that even if these ratios between the residues are not respected, for example in the case when the species contains a residue mixture, the yield will go down but the final products will be separable by a method known by a person skilled in the art, for example fractional distillation or column chromatography.

c) The species must also be selected advantageously so as to maximize, i.e. have at least 30% of cleavable bonds relative to the total number of bonds present between the monomer units in the lignin. In the sense of the invention, "cleavable bonds" means the sp$^3$ carbon-oxygen bonds that will be cleavable by the depolymerization step and that lead to cleavage of all the linkages between two successive monomer entities present in lignin. In the context of the present invention, selective cleavage of the sp$^3$ carbon-oxygen bonds means the bonds of types β-O-4 and α-O-4. In the method of the invention, the lignin employed may be, for example, a lignin containing at least 30% of bonds of the β-O-4 type and/or at least 3% of α-O-4 bonds. In the case of the lignin in wood, the bonds of types β-O-4 and α-O-4 constitute between 40 and 60% of the bonds present. The percentages indicated correspond to the percentage of one type of bond relative to the total number of bonds present between the monomer units in the lignin. This percentage can be determined by NMR or pyrolysis, for example.

Lignin also comprises bonds that are modifiable but not cleavable, such as the bonds β-5, β-1, β-β. The lignin depolymerization step in the method of the invention modifies these bonds but a linkage is still preserved between the aromatic monomers in lignin. Finally, the third category of bonds groups together the bonds that are not cleavable and are not modifiable, such as the bonds 4-O-5, 5-5. In the context of the present invention, these bonds are inert and remain intact in the operating conditions applied. It is therefore important to select a lignin with as many cleavable bonds as possible (at least 30% of cleavable bonds relative to the total number of bonds present between the monomer units in the lignin) so as to be able to perform successful depolymerization of lignin into fragments similar to the starting monolignols as shown in FIG. 1.

The plant species is preferably selected so as to increase the cleavable β-O-4 and α-O-4 bonds and so as to have one predominant type of residue H, G or S in the lignin.

Thus, the plant species is preferably selected so as to have:

at least 10 wt % of lignin relative to the total weight of the sample of the plant species selected;

at least 30% of cleavable bonds relative to the total number of bonds present between the monomer units in the lignin; and at least 50% of residue G, H or S of the total number of residues present in the lignin used.

The plant species may be selected for example from cedars, pines, spruces, firs with the aim of forming a molecule containing 1 or 2 aromatic rings having a structure derived from unit G; or poplars, oaks, eucalyptus with the aim of generating a molecule containing 1 or 2 aromatic rings having a structure derived from unit S.

Once the plant species has been selected, it must be treated so as to extract the lignin. In the sense of the invention, the method of extraction of lignin denotes any physical and chemical technique for extracting, isolating, separating, or preparing lignin. As an example, we may mention the Kraft process (producing Kraft lignin), the sulfite process (producing lignosulfonates), the organosolv processes, which correspond to the methods using one or more organic solvents to extract the lignin (i.e. the following methods: Acetocell, Alcell, Acetosolv, ASAM, Organocell, Milox, Formacell, Batelle/Geneva phenol), the Steam-explosion method, the Klason method, the soda-AQ method (producing soda lignin or alkaline lignin), the method of biological extraction of lignin by biological organisms such as bacteria and enzymes, and the method of extracting lignin by acid hydrolysis.

The organosolv processes are described in the following references:

a) Alcell: J. H. Lora, W. G. Glasser, *J Polym Environ*, 2002, 10, 39-48;

b) Acetocell: Bojan Jankovic, *Bioresource Technol.*, 2011, 102, 9763-9771;

c) Acetosolv: J. C. Parajo, J. L. Alonso, D. Vazquez, *Bioresource Technology*, 1993, 46, 233-240;

d) ASAM: I. Miranda, H. Pereira, *Holzforschung*, 2002, 56, 85-90;

e) Batelle/Geneva phenol: A. Johansson, O. Aaltonen, P. Ylinen, *Biomass* 1987, 13, 45-65;

f) Formacell: X. F. Sun, R. C. Sun, P. Fowler, M. S. Baird, *Carbohydr. Polym.*, 2004, 55, 379-391;

g) Milox: P. Ligero, A. Vega, J. J. Villaverde, *Bioresource Technol.*, 2010, 101, 3188-3193;

h) Organocell: A. Lindner, G. Wegener, *J. Wood Chem. Technol.* 1988, 8, 323-340.

In the case of wood, the aforementioned methods of extraction allow separation of the three main constituents of wood: cellulose, hemicellulose and lignin. The aforementioned methods are mainly based on chemical or thermochemical transformations, leading to modification of the structure of the lignin extracted. This means that wood obtained from one and the same species may give rise to different lignin structures, depending on the method of extraction used.

The method of extraction of lignin is selected so as to modify the structure of the initial lignin present in the species as little as possible.

Thus, the lignin resulting from the extraction process keeps the same types of functionalities and the same proportions of the bonds as those present in the starting lignin. This helps to increase the overall yield of the method of the invention as well as selectivity relative to a given molecule containing 1 or 2 aromatic rings. The method of extraction in the present invention is preferably selected from the methods of the organosolv type that give lignins whose structure is very close to that of the initial lignin present in the species.

In the context of the invention, the method of extraction of lignin may also include the methods of treatment of lignin with the aim of introducing chemical functionalities, altering the physical properties and/or changing the average molecular weight of the lignin. Lignin is a polymer formed by a distribution of polymeric fragments having different molecular weights. The average molecular weight of lignin therefore corresponds to the average of the weights of these polymeric fragments; it can be calculated relative to the weight of the fragments or relative to their numbers. These methods of treatment may improve the yield and selectivity of the method of the invention. Thus, at the end of the aforementioned methods of extraction, the lignin may be treated in order to modify the ratio of the residues H, G and S of which it is constituted. This modification may also, in certain cases, lead to enrichment with a given residue and/or with a given type of bond, then increase in selectivity as well as yield, reducing the purification steps leading to the final monocyclic aromatic compound. It should be noted that lignins that were functionalized at the end of extraction (for example, Kraft lignin and lignosulfonates) may, after a defunctionalization reaction (for example, a desulfurization reaction), be used in the method of the invention in order to lead selectively to a pure molecule containing 1 or 2 aromatic rings, i.e. purity greater than or equal to 90 wt %, preferably between 90 and 99.9 wt %, relative to the total weight of the molecules containing 1 or 2 aromatic rings.

Whatever method is used for extracting and/or treating lignin, it is essential that the lignin obtained is free from sulfur, i.e. it contains a level of sulfur below 1.5 wt %, relative to the total weight of lignin. In fact, the inventors observed, quite unexpectedly, that when lignin contains a level of sulfur greater than or equal to 1.5 wt %, relative to the total weight of the lignin, lignin depolymerization by the method of the invention does not take place or is partial. When depolymerization is partial, it leads to molecules with an average molar mass by weight above 1500 g/mol for the molecules in silylated form or with an average molar mass by weight less than or equal to 450 g/mol, preferably less than or equal to 400 g/mol (i.e. molecules in which all the O—Si bonds have been cleaved, for example by hydrolysis). The level of sulfur in the lignin employed in the method of the invention is therefore advantageously greater than or equal to zero and remains below 1.5 wt %, relative to the total weight of the lignin, as defined below:

$$0 \leq \text{level of sulfur in the lignin} < 1.5 \text{ wt \%},$$

relative to the total weight of lignin.

The level of sulfur can be determined by the physical and chemical techniques known by a person skilled in the art, for example elemental analysis, analysis by ion-exchange chromatography, by infrared spectrophotometry, by oxidation of the sulfur to $SO_2$ then determination of the latter by the techniques known by a person skilled in the art, for example acidimetric analysis, iodometric analysis, or complexometric analysis.

According to a preferred variant of the invention, in the silane compound of formula (I), $R^1$, $R^2$ and $R^3$ represent, independently of one another, a hydrogen atom, an alkyl group, an alkoxy group, an amino group, an aryl group, a silylated group of formula [—$Si(X)_3$] with X as defined above with at least one of the X representing several siloxy groups, said siloxy groups may be repeated several times so as to lead to polymeric organosilanes of general formula

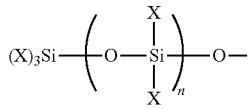

in which n is an integer between 1 and 20000, advantageously between 1 and 5000, more advantageously between 1 and 1000,
said alkyl, alkoxy and aryl groups optionally being substituted.

More preferably, in the silane compound of formula (I), $R^1$, $R^2$ and $R^3$ represent, independently of one another, a hydrogen atom; an alkyl group selected from the methyl, ethyl, propyl, butyl, pentyl, hexyl, heptyl groups and their branched isomers; an alkoxy group whose alkyl group is selected from the methyl, ethyl, propyl, butyl, pentyl, hexyl, heptyl groups and their branched isomers; an aryl group selected from the benzyl and phenyl groups; a silylated group as described above selected from polydimethylsiloxane (PDMS), polymethylhydroxysiloxane (PMHS) and tetramethyldisiloxane (TMDS).

Catalyst, in the sense of the invention, means any compound capable of modifying, notably increasing, the rate of the chemical reaction in which it participates, and which is regenerated at the end of the reaction. This definition includes both the catalysts, i.e. compounds that exert their catalytic activity without needing to undergo any modification or conversion, and the compounds (also called precatalysts) that are added to the reaction mixture, where they are converted into a catalyst.

It is in particular necessary for the catalyst to be selected taking into account notably its steric hindrance, its capacity for activating the silane and its solubility in the reaction mixture.

In the method of the invention, the catalyst may be an organic catalyst selected from:
the carbocations of formula $(X^1)_3C^+$ with $X^1$ representing a hydrogen atom, an alkyl group, an aryl group, an alkoxy group, a silyl group, a siloxy group and a halogen atom, as defined above, said carbocations being selected from the trityl cation $((C_6H_5)_3C^+)$, tropilium $(C_7H_7)^+$, the benzyl cation $(C_6H_5CH_2^+)$, the allyl cation $(CH_3—CH^+—CH=CH_2)$, methylium $(CH_3^+)$, cyclopropylium $(C_3H_5^+)$, the cyclopropyl carbocation of formula $C_3H_5—C^+R^1R^2$ with $R^1$ and $R^2$ as defined above, said carbocation being selected from the dimethyl cyclopropyl carbocation and the dicyclopropyl carbocation, acylium $(R^1—C=O)^+$ with $R^1$ as defined above selected from methyl, propyl and benzyl, the benzenium cation $(C_6H_5)^+$, the norbornyl cation $(C_7H_{11})^+$;
the oxoniums selected from $(CH_3)_3O^+BF_4^-$ (Meerwein salt) and $(CH_3CH_2)_3O^+BF_4^-$;
a silylium ion $(R^1)_3Si^+$ with $R^1$ as defined above, for example selected from $Et_3Si^+$ and $Me_3Si^+$;
the disilyl cations, preferably the disilyl cations having a bridging hydride selected from the formulas given below

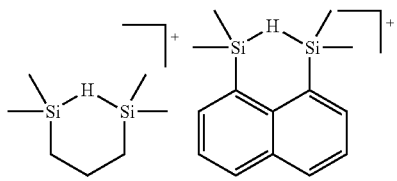

it being possible for said disilyl cations to be synthesized by a person skilled in the art as described by R. Panisch, M. Bolte, and T. Muller, *J. Am. Chem. Soc.* 2006, 128, pages 9676-9682).

The aforementioned carbocations are available commercially or can easily be synthesized by a person skilled in the art by various methods of synthesis, for example: the cation pool method, the internal redox method, the method using a leaving group, the methods using Lewis or Brønsted acids. These methods are described in the following references: R. R. Naredla and D. A. Klumpp, *Chem. Rev.* 2013, 113, pages 6905-6948; M. Saunders and H. A. Jimenez-Vazquez, *Chem. Rev.* 1991, 91, pages 375-397.

It should be noted that the anionic counterion of the silylium ion, of the carbocations and of the disilyl cations mentioned above is preferably a halide selected from $F^-$, $Cl^-$, $Br^-$ and $I^-$, or an anion selected from $BF_4^-$, $SbF_6^-$, $B(C_6F_5)_4^-$, $B(C_6H_5)_4^-$, $TfO^-$ or $CF_3SO_3^-$, $PF_6^-$.

In the method of the invention, the catalyst may also be organometallic. In this case we may mention the iridium complexes $([(PX^2CX^2P)Ir(R^7)(S)]^+Y^-)$, of formula (III)

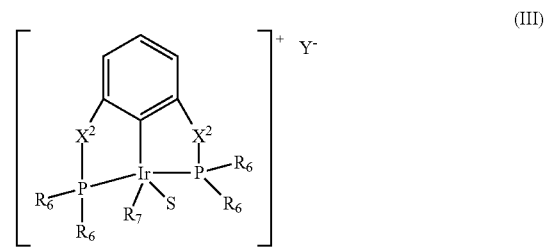

in which
$R^6$ represents an alkyl or aryl group as defined above, and preferably an isobutyl group;
$R^7$ represents a hydrogen atom or an alkyl group as defined above, and preferably a hydrogen atom; and
$X^2$ represents a —$CH_2$— group or an oxygen atom, and preferably an oxygen atom;
Y represents a counterion selected from $B(C_6F_5)_4$ and $B(C_6H_5)_4$, and preferably $B(C_6F_5)_4$;
S represents a molecule of solvent, coordinated to the complex, selected from dimethylsulfoxide (DMSO), acetonitrile ($CH_3CN$) and acetone ($CH_3COCH_3$), and preferably acetone.

According to a preferred embodiment of the invention, the iridium catalyst is $[(POCOP)Ir(H)(acetone)]^+B(C_6F_5)_4^-$ with (POCOP) representing 2,6-bis(di-tert-butylphosphinito)phenyl. This catalyst may be prepared by the methods described by I. Gottker-Schnetmann, P. White, and M. Brookhart, *J. Am. Chem. Soc.* 2004, 126, pages 1804-1811; and by J. Yang and M. Brookhart, *J. Am. Chem. Soc.* 2007, 129, pages 12656-12657.

In the method of the invention, the catalyst may also be organometallic. In this case we may mention the ruthenium complexes of formula (IV)

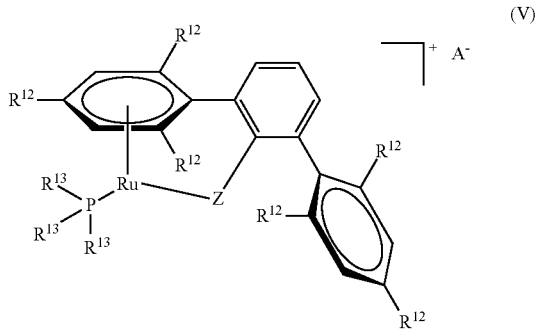

(V)

in which

R$^{12}$ represents a hydrogen atom or an alkyl group as defined above, R$^{12}$ preferably being a methyl group;

R$^{13}$ represents an aryl or an alkyl group as defined above, said aryl and alkyl groups optionally being substituted, R$^{13}$ preferably being p-FC$_6$H$_4$;

Z represents a —CH$_2$— group, an oxygen atom or a sulfur atom, Z preferably being a sulfur atom; and A$^-$ represents a counterion selected from B(C$_6$F$_5$)$_4$$^-$ and [CHB$_{11}$H$_5$Cl$_6$]—, A$^-$ preferably being B(C$_6$F$_5$)$_4$$^-$.

This type of catalyst may be prepared by the methods described by T. Stahl, H. F. T. Klare, and M. Oestreich, *J. Am. Chem. Soc.*, 2013, 135, pages 1248-1251.

The catalyst may also be of the Lewis acid type selected from the organometallic and metallic catalysts:

the boron compounds of formula B(X$^3$)$_3$ with X$^3$ representing a hydrogen atom, an alkyl group, an aryl group, an alkoxy group as defined above, said boron compounds being selected from BF$_3$, BF$_3$(Et$_2$O), BCl$_3$, BBr$_3$, triphenyl hydroborane, tricyclohexyl hydroborane, B(C$_6$F$_5$)$_3$, B-methoxy-9-borabicyclo[3.3.1]nonane (B-methoxy-9-BBN), B-benzyl-9-borabicyclo[3.3.1]nonane (B-benzyl-9-BBN);

the borenium compounds R$^1$R$^2$B$^+$ with R$^1$ and R$^2$ as defined above, said borenium compounds being for example Me-TBD-BBN$^+$, the borenium ferrocene derivatives corresponding to the formula

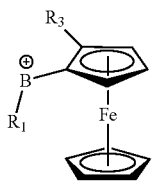

borenium ferrocene in which R$^1$ and R$^3$ are as defined above, for example R$^1$ is a phenyl group and R$^3$ is 3,5-dimethylpyridyl;

the aluminum compounds selected from AlCl$_3$, AlBr$_3$, aluminum isopropoxide Al(O-i-Pr)$_3$, aluminum ethanoate (Al(C$_2$H$_3$O$_2$)), Krossing's salt [Ag(CH$_2$Cl$_2$)]{Al[OC(CF$_3$)$_3$]$_4$}, Li{Al[OC(CF$_3$)$_3$]$_4$}, the cationic aluminum compounds of formula (X$^4$)$_2$Al$^+$ where X$^4$ is a halogen atom, an alkoxy group, an alkyl group as defined above, for example Et$_2$Al$^+$;

the indium compounds selected from InCl$_3$, In(OTf)$_3$;
the iron compounds selected from FeCl$_3$, Fe(OTf)$_3$;
the tin compounds selected from SnCl$_4$, Sn(OTf)$_2$;
the phosphorus compounds such as PCl$_3$, PCl$_5$, POCl$_3$;
the trifluoromethanesulfonate or triflate compounds (CF$_3$SO$_3$$^-$) of transition metals and lanthanides selected from scandium triflate, ytterbium triflate, yttrium triflate, cerium triflate, samarium triflate, neodymium triflate.

In the context of the present invention, OTf$^-$ represents the triflate or trifluoromethanesulfonate ion of formula CF$_3$SO$_3$$^-$: the terms triflate or trifluoromethanesulfonate, OTf$^-$ or CF$_3$SO$_3$ may therefore be used synonymously to denote the same entity.

Preparation of the borenium ferrocene derivatives is described by J. Chen, R. A. Lalancettea and F. Jäkle, *Chem. Commun.*, 2013.49, pages 4893-4895; preparation of Krossing's salts is described by I. Krossing, *Chem.-Eur. J.*, 2001, 7, page 490; and preparation of Et$_2$Al$^+$ is described by M. Khandelwal and R. J. Wehmschulte, *Angew. Chem. Int. Ed.* 2012, 51, pages 7323-7326.

According to a preferred variant of the invention, the catalyst is an organometallic catalyst selected from BF$_3$; InCl$_3$; triphenylcarbenium tetrakis(perfluorophenyl)borate [(Ph)$_3$C$^+$B(C$_6$F$_5$)$_4$$^-$,B(C$_6$F$_5$)$_3$].

Figure 7:
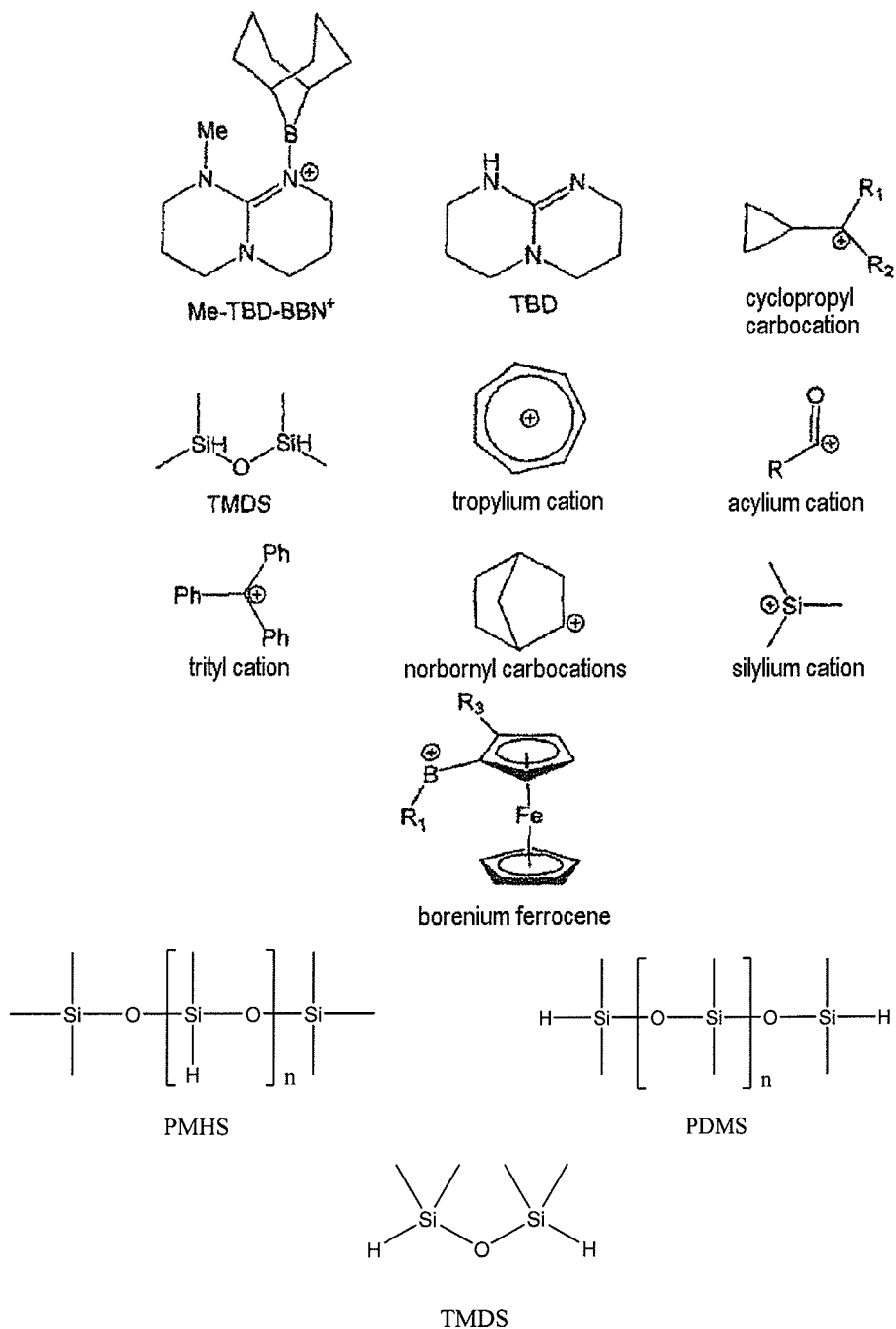
FIG. 7 illustrates some abbreviations used according to embodiments of the present disclosure.

Some of the abbreviations used in the context of the invention are shown in FIG. 7.

The catalysts may, if necessary, be immobilized on heterogeneous supports in order to ensure easy separation of said catalyst and/or recycling thereof. Said heterogeneous supports may be selected from supports based on silica gel and plastics, for example polystyrene; carbon-containing supports selected from carbon nanotubes; silicon carbide; alumina; and magnesium chloride (MgCl$_2$).

In the method according to the invention, the reaction may take place under a pressure of an inert gas or a mixture of inert gases selected from nitrogen and argon, or of the gases generated by the process, notably methane and hydrogen. The pressure may be between 0.2 and 50 bar, preferably between 0.2 and 30 bar, more preferably between 1 and 20 bar, inclusive.

The reaction temperature may be between 0 and 150° C., preferably between 0 and 125° C., more preferably between 25 and 70° C., inclusive.

The reaction time depends on the degree of conversion of the silane compound of formula (I), the nature of the lignin as well as the desired degree of silylation.

The reaction may be carried out for a time from 1 minute to 200 hours, advantageously from 1 minute to 48 hours, preferably from 10 minutes to 48 hours, inclusive.

The method of the invention, in particular the reaction between the various reactants, may take place in a solvent or a mixture of at least two solvents selected from:

silylated ethers, preferably selected from 1,1,1,3,3,3-hexamethyldisiloxane ((Me$_3$Si)$_2$O), 1,1,1,3,3,3-hexaethyldisiloxane ((Et$_3$Si)$_2$O).

hydrocarbons, preferably selected from benzene, toluene, pentane and hexane;

sulfoxides, preferably selected from dimethylsulfoxide (DMSO);

alkyl halides, preferably selected from chloroform, methylene chloride, chlorobenzene, dichlorobenzene.

The silanes of formula (I) and the catalysts used in the method of the invention are generally commercial compounds or may be prepared by the methods known by a person skilled in the art.

The weight ratio between the silane compound of formula (I) and the lignin depends on the type of lignins used and the type of final molecules desired (production of the silylated ethers of type IIb, IId, IIf as represented in the examples or production of the silylated ethers of type IIa, IIc, IIe as represented in the examples). Compounds IIa-IIf are therefore silylated ethers, which can be deprotected to give the corresponding alcohols of formula (IV) by hydrolysis. Hydrolysis of the silylated ethers may be carried out by the techniques of chemical hydrolysis (acid or basic conditions) known by a person skilled in the art. Enzymatic hydrolysis may also be employed. Examples of hydrolysis are given in the embodiment examples of the method of the invention.

The silylated ethers containing a substituted propyl chain of formula IIb, IId, IIf may also give other silylated ethers containing an unsubstituted propyl chain of type IIa, IIc, IIe by the same method as that used for lignin depolymerization. As the depolymerization process reduces the $sp^3$ carbon-oxygen bonds, the silylated bonds (—C—O—Si—) may easily be reduced to alkane (—C—H). Production of the silylated ethers containing an unsubstituted propyl chain will depend on the number of equivalents of silane compound of formula (I) added.

Thus, in the context of the present invention, the weight ratio of the silane compound of formula (I) to lignin may be between 0.5 and 6, preferably between 1 and 4, inclusive.

The amount of catalyst used in the method of the invention is from 0.001 to 1 equivalent by weight, preferably from 0.001 to 0.9 equivalent by weight, more preferably from 0.01 to 0.9 equivalent by weight, even more preferably from 0.01 to 0.5 equivalent by weight, inclusive, relative to the initial weight of lignin.

As already stated, depolymerization of lignin leads to the production of aromatic molecules containing 1 or 2 aromatic rings with an average molar mass by weight below 1500 g/mol for the molecules in silylated form or with an average molar mass by weight less than or equal to 450 g/mol, preferably less than or equal to 400 g/mol (i.e. a degree of polymerization less than 3 monomer units, preferably between 1 and 2 monomer units). The weight-average molecular weight of the aromatic compounds and the degree of polymerization of the lignin can be determined by the usual techniques employed in this field and known by a person skilled in the art, for example size exclusion chromatography.

After depolymerization, the resultant aromatic compounds are generally at least partially in silylated form, in particular on the phenolic residues of the lignin. However, simple hydrolysis in conditions familiar to a person skilled in the art leads to the corresponding aromatic compounds in their nonsilylated forms.

In the context of the present invention, hydrolysis means a method of transformation of the siloxy groups present in silylated aromatic compounds resulting from the depolymerization of lignin, into hydroxyl groups, by a desilylation reaction. This transformation may be carried out in acid or basic conditions or else in the presence of fluoride ions, these conditions being familiar to a person skilled in the art. In the context of the present invention, the method of hydrolysis is preferably selected from: HCl or $H_2SO_4$ 2 M in THF; NaOH or KOH 10% in a water/THF mixture; tetra-n-butylammonium fluoride (TBAF) 1 M in THF.

Simple filtration may allow recovery of the, optionally supported, catalyst and removal of any byproducts.

Thus, the method of the invention allows lignin to become the main source of aromatic compounds of biological origin for the chemical industry. Aromatic compounds of high added value, for example benzene, toluene, the xylenes (BTX), the substituted coniferols, phenol, the aromatic polyols, and the quinines may thus be obtained and used in the synthesis of phenol-formaldehyde resins, polyolefin-lignin polymers, polyester-lignin polymers, polyurethanes, bioplastics, and epoxy resins.

The aromatic compounds obtained by the method of the invention can therefore be used as raw materials in the construction sector, the perfumes industry, the petrochemical, food, electronic, textile, aeronautical, pharmaceutical, cosmetic, and agrochemical industries.

The invention therefore relates to the use of the method of depolymerizing lignin according to the invention, in the manufacture of fuels, electronic components, plastics, rubber, medicinal products, vitamins, cosmetics, perfumes, food products, synthetic yarn and fibers, synthetic leather, adhesives, pesticides, and fertilizers.

The invention also relates to a method of manufacturing fuels, electronic components, plastics, rubber, medicinal products, vitamins, cosmetics, perfumes, food products, synthetic yarn and fibers, synthetic leather, adhesives, pesticides, and fertilizers, characterized in that it comprises a step of depolymerization of lignin by the method according to the invention.

Besides good productivity and good selectivity, the method of the invention makes it possible to use
lignin, which is the largest reservoir of aromatic compounds of biological origin, and
a mild reducing agent (silane of formula (I)) that is stable in air and inexpensive, and is compatible with the possible presence of functional groups on the lignin.

The method of the invention allows lignin to become the main source of aromatic compounds of biological origin for the chemical industry.

Other advantages and features of the present invention will become clear on reading the following examples, given for purposes of illustration, and nonlimiting.

EXAMPLES

The method of depolymerizing lignin by selective cleavage of the $sp^3$ carbon-oxygen bond of the alkaryl ethers present in lignin is carried out in the presence of a catalyst, by reacting a lignin with a level of sulfur below 1.5 wt % of lignin, with a silane compound of formula (I) according to the following experimental protocol.

The reactants used, notably the silane compound of formula (I) and the catalyst, are commercial products.

General Experimental Protocol for Depolymerization of Lignin
1. Under an inert atmosphere of argon or nitrogen, the silane compound of formula (I), the catalyst (from 1 to 0.001 equivalents by weight calculated relative to the initial weight of lignin added) and half the amount of solvent are stirred in a glass vessel of suitable volume. The concentration of silane in the reaction mixture is in the range 1.0-6.0 mol·$L^{-1}$ (concentration calculated on the basis of half the final volume of solvent introduced).
2. In addition, in a Schlenk tube, organosolv lignin (10-40% of equivalent by weight of silane added), previously dried overnight using a vacuum manifold, is stirred with the remaining half of solvent.
3. The solution containing the catalyst and the silane compound of formula (I) is added slowly (addition time 15 minutes to 1 hour), using a syringe and with stirring, to the Schlenk tube. The latter is left open for evacuating the gases produced by the reaction.

4. After the end of adding the solution, and when release of gases has stopped, the Schlenk tube is closed and is stirred. The starting lignin is then almost completely soluble. The reaction is monitored by GC-MS.
5. Once the reaction has ended (reaction time from 1 to 72 hours), the solvent as well as the volatile compounds are evaporated using a vacuum manifold ($10^{-2}$ mbar). The viscous liquid obtained is purified by silica gel chromatography using an elution gradient from 100:0 to 0:100 of pentane: $CH_2Cl_2$ for the nonpolar fractions, and an elution gradient from 100:0 to 0:100 of $CH_2Cl_2$: EtOAc for the polar fractions. When a fraction is very polar, elution may be performed with EtOAc:MeOH H mixture (50:50 to 0:100). It should be noted that depending on the intended application, the purification step may or may not be omitted.
6. Finally, the various fractions from the column are hydrolyzed in an acid medium using HCl or $H_2SO_4$ 2M in THF, or in a basic medium using NaOH or KOH 15 to 30 wt %, or finally using a fluorinated reactant of the type: HF-pyridine, TBAF, CsF, $NH_4F$ to give the corresponding hydrolyzed product.

A set of results is presented below, giving examples of depolymerization of organosolv lignin.

The catalysts tested are $B(C_6F_5)_3$ as well as the iridium complex ([(POCOP)Ir(H)(acetone)]$^+$B($C_6F_5$)$_4^-$) whose synthesis is described by I. Gottker-Schnetmann, P. White, and M. Brookhart, *J. Am. Chem. Soc.* 2004, 126, pages 1804-1811; and by J. Yang and M. Brookhart, *J. Am. Chem. Soc.* 2007, 129, pages 12656-12657.

The lignin used is obtained from several methods of the organosolv type {a) Alcell: J. H. Lora, W. G. Glasser, *J Polym Environ,* 2002, 10, pages 39-48; b) Acetocell: Bojan Jankovic, *Bioresource Technol.,* 2011, 102, pages 9763-9771; c) Acetosolv: J. C. Parajo, J. L. Alonso, D. Vazquez, *Bioresource Technology,* 1993, 46, pages 233-240; d) ASAM: I. Miranda, H. Pereira, *Holzforschung,* 2002, 56, pages 85-90; e) Batelle/Genevaphenol: A. Johansson, O. Aaltonen, P. Ylinen, *Biomass* 1987, 13, pages 45-65; f) Formacell: X. F. Sun, R. C. Sun, P. Fowler, M. S. Baird, *Carbohydr. Polym.,* 2004, 55, pages 379-391; g) Milox: P. Ligero, A. Vega, J. J. Villaverde, *Bioresource Technol.,* 2010, 101, pages 3188-3193; h) Organocell: A. Lindner, G. Wegener, *J. Wood Chem. Technol.* 1988, 8, pages 323-340} and in particular the AVIDEL process (described by H. Q. Lam, Y. Le Bigot, M. Delmas, G. Avignon, *Industrial Crops and Products,* 2001, 14, pages 139-144), which constitutes an optimized version of the Formacell method.

The types of wood from which the lignins are obtained are selected with different G/H/S proportions, and in addition a mixture of several types of wood was used, to demonstrate the versatility and robustness of the method. In the context of the invention, "robustness of the method" means a method which, in very mild operating conditions, allows cleavage of the chemical functions that are usually very difficult to cleave.

Example 1: Depolymerization of Lignin Obtained from London Plane (*Platanus acerifolia*) (Extracted by the AVIDEL Process) Using Triethylsilane ($Et_3SiH$)

The depolymerization of London plane is carried out following the general procedure for depolymerization described above.

Depolymerization is carried out with 4-5 mol·$L^{-1}$ $Et_3SiH$ as silane (concentration calculated on the basis of half the final volume of solvent introduced). The weight of lignin added corresponds to 30% of the weight of silane added and the solvent used is dichloromethane ($CH_2Cl_2$). The reaction takes place in the presence of 20-30 wt % of catalyst (weight calculated relative to the weight of lignin added). The catalyst used is $B(C_6F_5)_3$.

The solution of silane and catalyst is added to the Schlenk tube over a period of 30 minutes and the reaction is stirred for 24 hours at 25° C. After the end of the reaction and evaporation of the solvent and volatiles, the viscous liquid obtained is purified using the same conditions as described above. This liquid consists of a mixture of products of formulas IIa, IIb, IIe and IId (identified by NMR and GC-MS).

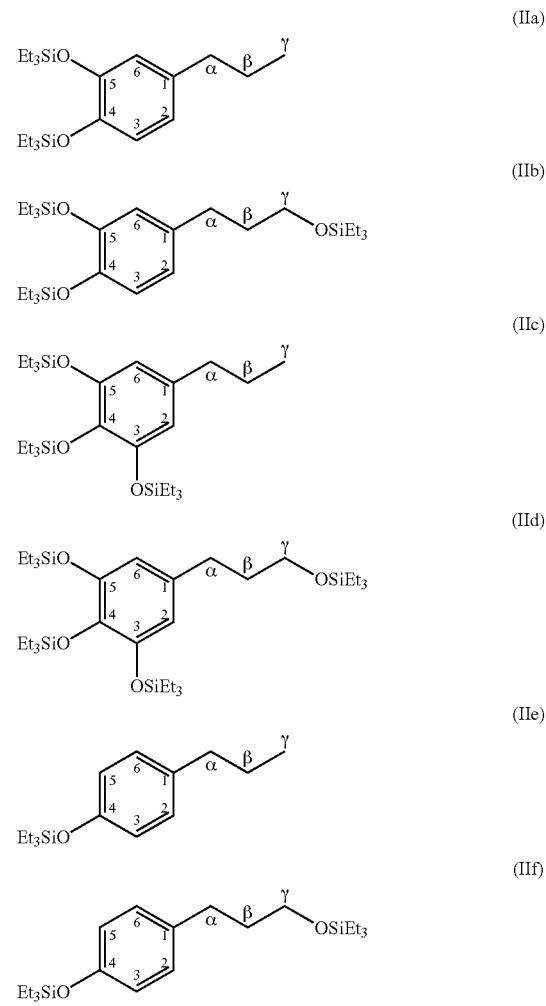

The molar ratio IIa/IIb/IIe/IId was determined according to GC-MS analysis (apparatus Shimadzu GCMS-QP2010 Ultra gas chromatograph mass spectrometer equipped with a fused silica capillary column Supelco SLB™-ms (30 m×0.25 mm×0.25 μm) as indicated in Table 1. Finally, the fractions from purification were hydrolyzed in an acid medium using a 2M HCl solution in THF. After stirring for 16 hours at room temperature (20±5° C.), the solvent and the volatiles are evaporated, giving the various corresponding polyols.

IIa:

$^1$H NMR (200 MHz, CDCl$_3$, Me$_4$Si) δ (ppm)=6.71 (1H, d, $^3$J=8.1 Hz, Ar—H), 6.63 (1H, s, Ar—H), 6.58 (1H, d, $^3$J=8.1 Hz, Ar—H), 2.45 (2H, t, $^3$J=7.8 Hz, Ar—CH$_2$), 1.57 (2H, sex, $^3$J=7.8 Hz, CH$_2$—CH$_3$), 0.98 (18H, t, $^3$J=7.9 Hz, CH$_3$CH$_2$Si), 0.90 (3H, t, $^3$J=7.8 Hz, CH$_3$CH$_2$Si), 0.74 (12H, q, $^3$J=7.9 Hz, CH$_3$CH$_2$Si).

$^{13}$C NMR (50 MHz, CDCl$_3$, Me$_4$Si): δ (ppm)=146.5, 144.7, 136.0, 121.3, 120.9, 120.2, 37.4, 24.7, 13.9, 6.9, 5.3, 5.2.

HR-MS (APPI): calculated (M+) (C$_{21}$H$_{40}$O$_2$Si$_2$), m/z 380.2566; found (M+), m/z 380.2559.

Anal. Calculated. for C$_{21}$H$_{40}$O$_2$Si$_2$ (molecular weight 380.72): C, 66.25; H, 10.59.

Found: C, 66.18; H, 10.46.

MS: IE (m/z): 380 (9); 351 (4); 207 (8); 117 (4); 116 (11); 115 (100); 88 (7); 87 (74); 59 (45); 58 (4).

IIb:

$^1$H NMR (200 MHz, CDCl$_3$, Me$_4$Si) δ (ppm)=6.79-6.50 (3H, m, Ar—H), 3.60 (2H, t, $^3$J=6.6 Hz, CH$_2$—O), 2.54 (2H, t, $^3$J=7.6 Hz, Ar—CH$_2$), 1.79 (2H, quin, $^3$J=7.0 Hz, Ar—CH$_2$—CH$_2$), 1.05-0.88 (27H, m, CH$_3$CH$_2$Si), 0.84-0.48 (18H, m, CH$_3$CH$_2$Si).

$^{13}$C NMR (50 MHz, CDCl$_3$, Me$_4$Si): δ (ppm)=146.5, 144.8, 135.4, 121.3, 120.9, 120.3, 62.3, 34.7, 31.5, 6.9, 6.8, 5.2, 5.2, 4.6.

MS: IE (m/z): 87 (100), 115 (57), 59 (38), 89 (28), 207 (24), 32 (16), 235 (11), 88 (10), 337 (9), 511 (8), 116 (6), 86 (6).

IIc:

$^1$H NMR (200 MHz, CDCl$_3$, Me$_4$Si) δ (ppm)=6.27 (2H, s, Ar—H), 2.39 (2H, t, $^3$J=7.5 Hz, Ar—CH$_2$), 1.69-1.45 (2H, m, CH$_2$—CH$_3$), 1.1-0.84 (27H, m, CH$_3$CH$_2$Si), 0.90-0.81 (3H, m, CH$_3$CH$_2$Si), 0.83-0.65 (18H, m, CH$_3$CH$_2$Si).

$^{13}$C NMR (50 MHz, CDCl$_3$, Me$_4$Si): δ (ppm)=147.8, 146.5, 134.5, 113.6, 37.7, 24.6, 13.7, 7.0, 6.8, 5.4, 5.2.

MS: IE (m/z): 510 (8); 339 (4); 338 (10); 337 (31); 116 (7); 115 (60); 88 (10); 87 (100); 86 (4); 59 (49).

IId:

$^1$H NMR (200 MHz, CDCl$_3$, Me$_4$Si) δ (ppm)=6.28 (2H, s, Ar—H), 3.59 (2H, t, $^3$J=6.7 Hz, CH$_2$—O), 2.48 (2H, t, $^3$J=7.5 Hz, Ar—CH$_2$), 1.78 (2H, quin, $^3$J=7.3 Hz, Ar—CH$_2$—CH$_2$), 1.13-0.85 (36H, m, CH$_3$CH$_2$Si), 0.84-0.49 (24H, m, CH$_3$CH$_2$Si).

$^{13}$C NMR (50 MHz, CDCl$_3$, Me$_4$Si): δ (ppm)=147.9, 136.6, 134.0, 113.6, 62.3, 34.6, 31.7, 6.9, 6.8, 5.4, 5.2, 4.5.

MS: IE (m/z): 87 (100), 115 (36), 59 (32), 89 (19), 641 (9), 88 (9), 467 (8), 365 (7), 337 (6), 642 (5), 640 (5), 116 (4).

Example 2: Depolymerization of Lignin from Pine (*Pinus pinea*) (Extracted by the AVIDEL Process) Using Triethylsilane (Et$_3$SiH)

The same procedure as used for depolymerization of lignin from London plane is used for depolymerization of lignin from pine. In this case, after purification, the product IIa is obtained with very high purity (>99.7%) with a yield by weight from 10 to 20% relative to the weight of lignin used (not optimized). This product was characterized by GC-MS, $^{13}$C NMR, $^1$H NMR and HR-MS. Finally, the fractions from purification are hydrolyzed by stirring each fraction at 25° C. for 16 h in the presence of a 2M HCl solution in THF. Finally, the polyols are obtained after evaporation of the solvent and the volatile compounds.

Example 3: Depolymerization of Lignin Obtained from Lombardy Poplar (*Populus nigra*) (Extracted by the AVIDEL Process) Using Triethylsilane (Et$_3$SiH)

The same procedure as used for depolymerization of lignin from London plane is used for depolymerization of lignin from Lombardy poplar. Moreover, the products obtained in both cases are similar. Among the most volatile products, the products of formulas IIa and IIc are identified by NMR and GC-MS as indicated in Table 1.

Example 4: Depolymerization of Lignin Obtained from Silver Birch (*Betula pendula*) (Extracted by the AVIDEL Process) Using Triethylsilane (Et$_3$SiH)

The same procedure as used for depolymerization of lignin from London plane is used for depolymerization of lignin from silver birch. Moreover, the products obtained in both cases are similar. Among the most volatile products, the products of formulas IIa and IIe are identified by NMR and GC-MS as indicated in Table 1.

Example 5: Depolymerization of Lignin Obtained from Common Beech (*Fagus Sylvatica*) (Extracted by the AVIDEL Process) Using Triethylsilane (Et$_3$SiH)

The same procedure as used for depolymerization of lignin from London plane is used for depolymerization of lignin from common beech. Moreover, the products obtained in both cases are similar. Among the most volatile products, the products of formulas IIa and IIe are identified by NMR and GC-MS as indicated in Table 1.

Example 6: Depolymerization of Lignin Obtained from Eucalyptus (*Eucalyptus camaldulensis*) (Extracted by the AVIDEL Process) Using Triethylsilane (Et$_3$SiH)

The same procedure as used for depolymerization of lignin from common beech is used for depolymerization of lignin from eucalyptus. Moreover, the products obtained in both cases are similar. Among the most volatile products, the products of formulas IIa, IIb, IIe and IId are identified by NMR and GC-MS. The IIc/IIa molar ratio is 76/24 respectively according to GC-MS analysis.

Example 7: Depolymerization of Lignin Obtained from Western Red Cedar (*Thuja plicata*) (Extracted by the AVIDEL Process) Using Triethylsilane (Et$_3$SiH)

The same procedure as used for depolymerization of lignin from eucalyptus (*Eucalyptus camaldulensis*) is used for depolymerization of lignin from western red cedar. Moreover, the products obtained in both cases are similar. Among the most volatile products, the products of formulas IIa and IIb were identified by NMR and GC-MS as indicated in Table 1.

Example 8: Depolymerization of Lignin Obtained from F315 Sawdust Mixture (Extracted by the AVIDEL Process) Using Tetramethyldisiloxane (TMDS)

Depolymerization of lignin is carried out with lignin obtained from F315 sawdust mixture (sawdust mixture marketed by the company SPPS extracted from species belonging to the family Pinaceae).

When TMDS (tetramethyldisiloxane) is used as silane, there is a possibility of formation of gel, which makes the reaction very difficult. In this case two solutions may be envisaged: dilution of the solution 3 to 4 times using $CH_2Cl_2$ as solvent or else use of benzene or toluene as solvent. However, reaction will be slower in both cases envisaged. If reaction takes place in $CH_2Cl_2$, the concentration of TMDS is of the order of 1-3 mol·$L^{-1}$ (concentration calculated on the basis of half the final volume of solvent introduced). 20 wt % of $B(C_6F_5)_3$ (weight calculated relative to the weight of lignin added) is required for catalyzing the reaction. The weight of lignin added is between 10 and 30% of the weight of silane added. Addition of the catalyst-silane mixture takes from 30 to 45 min. Then the reaction is stirred for 24 hours at 25° C.

After the end of the reaction, the volatile compounds as well as the solvent are evaporated under vacuum ($10^{-2}$ mbar). The mixture resulting from depolymerization degrades during purification on a silica column and the product obtained is hydrolyzed in a basic medium, using a mixture of THF and $H_2O$ containing 10 wt % of NaOH. After 16 hours of stirring at 25° C., the volatile compounds as well as the solvents are evaporated, and the product is purified on a silica column. Hydrolysis of the mixture leads to products of formula (IV).

Example 9: Depolymerization of Lignin Obtained from the Commercial F315 Sawdust Mixture (Extracted by the AVIDEL Process) Using ([(POCOP)Ir(H)(acetone)]$^+$B($C_6F_5$)$_4^-$) and Triethylsilane ($Et_3SiH$)

Depolymerization of lignin obtained from F315 sawdust mixture (sawdust mixture marketed by the company SPPS extracted from species belonging to the family Pinaceae) is carried out following the general operating protocol for depolymerization described above.

When the ([(POCOP)Ir(H)(acetone)]$^+$B($C_6F_5$)$_4^-$) complex is used for lignin depolymerization, the procedure is similar to that in which the catalyst used is $B(C_6F_5)_3$. $Et_2SiH_2$ (5 mol·$L^{-1}$) is used as silane in chlorobenzene. The weight of the lignin corresponds to 30% of the weight of silane added. The reaction takes place in the presence of 25 wt % of catalyst (weight calculated relative to the weight of lignin added). Addition of the silane and catalyst takes 30 min. The reaction time is of the order of 24 hours. Then the solvent and the volatiles are evaporated, and the viscous liquid obtained is purified on a silica column (see general procedure). The products from the column are hydrolyzed by stirring the products for 16 hours in a 2M HCl solution in THF. Finally, the various corresponding polyols are obtained by evaporation of the solvent and volatiles under vacuum. Hydrolysis of the mixture leads to products of formula (IV).

Example 10: Depolymerization of Lignin Obtained from F315 Sawdust Mixture (Rich in G Unit) (Extracted with Ethanol) with Triethylsilane ($Et_3SiH$)

Lignin obtained from F315 sawdust mixture (sawdust mixture marketed by the company SPPS extracted from species belonging to the family Pinaceae) was extracted with ethanol in the presence of a catalytic amount of hydrochloric acid, by the method described by S. Bauer, H. Sorek, V. D. Mitchell, A. B. Ibáñez, D. E. Wemmer, *J. Agric. Food Chem.* 2012, 60, pages 8203-8212.

The same procedure as used for depolymerization of lignin from plane is used. This method leads to complete dissolution of the lignin as well as production of a mixture of products.

Among the most volatile products, IIa and IIb are identified by NMR and GC-MS as indicated in Table 1. Hydrolysis of the mixture leads to products of formula (IV).

Example 11: Depolymerization of Lignin Obtained from F315 Sawdust Mixture (Rich in G Unit) (Extracted with Methanol) with Triethylsilane ($Et_3SiH$)

Lignin from F315 sawdust mixture (sawdust mixture marketed by the company SPPS extracted from species belonging to the family Pinaceae) was extracted with methanol, by the method described by K. Barta, G. R. Warner, E. S. Beach, P. T. Anastas, *Green Chem.*, 2014, 16, pages 191-196.

The same procedure is used as for depolymerization of lignin from plane. This method leads to complete dissolution of the lignin and its depolymerization, generating a mixture of products.

Among the most volatile products, IIa and IIb are identified by NMR and GC-MS as indicated in Table 1. Hydrolysis of the mixture leads to products of formula (IV).

Example 12: Depolymerization of Lignin Obtained from F315 Sawdust Mixture (Rich in G Unit) (Extracted with Acetone) with Triethylsilane ($Et_3SiH$)

Lignin from F315 sawdust mixture (sawdust mixture marketed by the company SPPS extracted from species belonging to the family Pinaceae) was extracted with acetone in the presence of a catalytic amount of hydrochloric acid, by the method described by S. Bauer, H. Sorek, V. D. Mitchell, A. B. Ibáñez, D. E. Wemmer, *J. Agric. Food Chem.* 2012, 60, pages 8203-8212.

The same procedure is used as for depolymerization of lignin from plane. This method leads to complete dissolution of the lignin as well as the production of a mixture of products of general formula II.

Among the most volatile products, IIb is identified by NMR and GC-MS as indicated in Table 1. Hydrolysis of the mixture leads to products of formula (IV).

Example 13 (Comparative): Depolymerization with Triethylsilane ($Et_3SiH$) of Commercial Lignin (Aldrich: Kraft Lignin) Obtained from Softwood and Desulfurized Using Soda The same procedure as for depolymerization of lignin from *eucalyptus* (*Eucalyptus camaldulensis*) is used for depolymerization of lignin from the Kraft process, having a level of sulfur of 3.76 wt % relative to the total weight of lignin. No dissolution or depolymerization was observed for this lignin. When this same sample of lignin is treated by the AVIDEL process again, the level of sulfur reaches 3 wt % relative to the total weight of the lignin, but depolymerization still does not take place. This means that the presence of sulfur in the reaction mixture plays a crucial role in deactivation of the reaction.

The compounds of formula (IV) obtained after hydrolysis of the silylated compounds resulting from the depolymerization of lignin are of formula (IV)

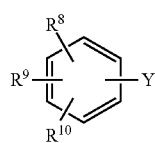
(IV)

in which $R^8$, $R^9$, $R^{10}$ represent, independently of one another, a hydrogen atom, a hydroxyl group;

Y represents an alkyl group, an alkenyl group, an alkynyl group, a carbonyl group —$CR^4$=O with $R^4$ representing a hydrogen atom, an alkyl group, a hydroxyl group, an alkoxy group, said alkyl, alkenyl and alkynyl groups optionally being substituted.

Table 1 summarizes the results of depolymerization of the lignins in the examples given above.

In Table 1:

% of lignin extracted denotes the percentage by weight of lignin extracted relative to the weight of wood used initially;

wt % denotes the percentage by weight of the species relative to the initial weight of lignin introduced evaluated by external calibration of GC-MS by the same molecules under analysis.

The operating conditions applied for obtaining the results in Table 1 are as follows: Lignin, $Et_3SiH$ (275 to 320 wt %/weight of lignin), $B(C_6F_5)_3$ (15 to 25 wt %/weight of lignin), $CH_2Cl_2$ (995 wt %/weight of lignin), 25° C., 16 hours.

| Source of lignin | Method used for extracting lignin | wt % of lignin extracted | wt % IIa | wt % IIc | wt % IIb | wt % IId |
|---|---|---|---|---|---|---|
| F315 (softwood) | methanol reflux | 2 | 15 | — | 1 | — |
| Stone pine (softwood) | AVIDEL | 8 | 16 | — | — | — |
| Western red cedar (hardwood) | AVIDEL | 7 | 8 | — | 2 | — |
| Common spruce (softwood) | AVIDEL | 6 | 16 | — | 18 | — |
| F315 (softwood) | ethanol reflux | 3 | 13 | — | 15 | — |
| F315 (softwood) | acetone reflux | 2 | — | — | 4 | — |
| Common beech (hardwood) | AVIDEL | 14 | 13 | 22 | — | — |
| Lombardy poplar (hardwood) | AVIDEL | 17 | 19 | 21 | — | — |
| Silver birch (hardwood) | AVIDEL | 13 | 10 | 26 | — | — |
| Holm oak (hardwood) | AVIDEL | 12 | 6 | 37 | — | 13 |
| Date palm (hardwood) | AVIDEL | 10 | 3 | 6 | 10 | 79 |
| Eucalyptus (hardwood) | AVIDEL | 9 | 8 | 30 | 17 | 35 |
| Green plum (hardwood) | AVIDEL | 18 | 20 | — | 3 | 26 |
| Plane (hardwood) | AVIDEL | 10 | — | 15.6 | 9 | 65 |
| Cedar of Lebanon (softwood) | AVIDEL | 6 | 14 | — | 3 | — |
| Nordmann fir (softwood) | AVIDEL | 20 | 2 | — | — | — |
| Gaboon ebony (hardwood) | AVIDEL | 7 | — | — | 6 | — |

Experimental Protocol for Hydrolysis of Silylated Aromatic Compounds Resulting from Reductive Depolymerization of Lignin nBu$_4$NF.3H$_2$O (315.5 mg, 2.1 mmol, 2.1 equiv) was added slowly (about 5 min), under argon, to a solution of IIa (380.7 mg; 1.0 mmol, 1 equivalent) in 4 mL of THF. The solution was stirred for 1 h at 20° C. Then the volatiles were evaporated under vacuum and 4 mL of dichloromethane was added. Finally, compound IIa was purified on a silica column using gradient elution from 50% dichloromethane to 50% ethyl acetate. Evaporation of the solvents gives 4-propyl-benzene-1,2-diol (141.5 mg; 0.9 mmol; 84%) in the form of a colorless oil.

Table 2 summarizes the results of hydrolysis of the silylated aromatic molecules IIa-IIf resulting from reductive lignin depolymerization of the lignins in the examples given above.

TABLE 2

| Silylated aromatic molecule | Amount of TBAF (equiv.) | Appearance | Yield isolated (%) |
| --- | --- | --- | --- |
| IIa | 2.1 | Colorless oil | 84 |
| IIb | 3.1 | Colorless oil | 86 |
| IIc | 3.1 | White powder or colorless crystals | 94 |
| IId | 4.1 | White gum | 82 |
| IIe | 1.1 | Colorless oil | 77 |
| IIf | 2.1 | White powder | 92 |

After hydrolysis, all the O—Si bonds are transformed to O—H.

The invention claimed is:

1. A method of depolymerizing lignin to molecules containing 1 or 2 aromatic rings, comprising selectively cleaving of the sp$^3$ carbon-oxygen bond of the alkaryl ethers of the β-O-4, α-O-4, β-5, β-1, and β-β type present in lignin, wherein
   a lignin with a level of sulfur below 1.5 wt %, relative to the total weight of the lignin, is reacted, in the presence of a catalyst, with
   a silane compound of formula (I)

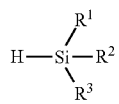

(I)

in which
   R$^1$, R$^2$ and R$^3$ represent, independently of one another, a hydrogen atom, a halogen atom, a hydroxyl group, an alkyl group, an alkenyl group, an alkynyl group, an alkoxy group, an aryloxy group, a silylated group, a siloxy group, an aryl group, an amino group, or combinations thereof, said alkyl, alkenyl, alkynyl, alkoxy, silylated, siloxy, aryl, and amino groups optionally being substituted, or
   R$^3$ is as defined above and R$_1$ and R$_2$, taken together with the silicon atom to which they are bound, form a silylated heterocycle, optionally substituted,
wherein the molecules containing 1 or 2 aromatic rings have an average molar mass by weight below 1500 g/mol for the molecules in silylated form, and an average molar mass by weight less than or equal to 450 g/mol for the non-silyated form, and wherein the catalyst is
an organic catalyst selected from the group consisting of:
   carbocations selected from the group consisting of trityl cation ((C$_6$H$_5$)$_3$C$^+$); tropilium (C$_7$H$_7$)$^+$; benzyl cation (C$_6$H$_5$CH$_2$$^+$); allyl cation (CH$_3$—CH$^+$—CH=CH$_2$); methylium (CH$_3$$^+$); cyclopropylium (C$_3$H$_5$$^+$); cyclopropyl carbocation selected from dimethyl cyclopropyl carbocation and dicyclopropyl carbocation; acylium (R$^1$—C=O)$^+$ with R$^1$ selected from methyl, propyl, and benzyl; the benzenium cation (C$_6$H$_5$)$^+$; and the norbornyl cation (C$_7$H$_{11}$)$^+$;
   oxoniums selected from the group consisting of (CH$_3$)$_3$O$^+$BF$_4$$^-$ and (CH$_3$CH$_2$)$_3$O$^+$BF$_4$$^-$;
   a silylium ion (R$^1$)$_3$Si$^+$, selected from the group consisting of Et$_3$Si$^+$ and Me$_3$Si$^+$;
   disilyl cations having a bridging hydride selected from the group consisting of the formulas shown below

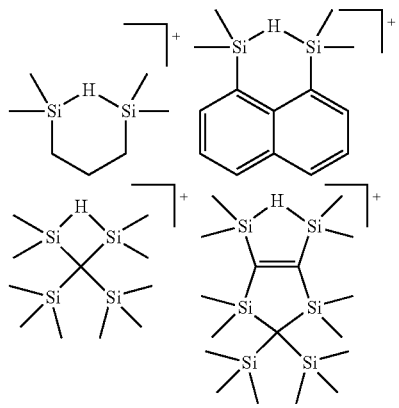

with the counterion of said silylium ion, of said carbocations and of said disilyl cations being
   a halide selected from the group consisting of F$^-$, Cl$^-$, Br$^-$ and I$^-$; or
   an anion selected from the group consisting of BF$_4$$^-$, SbF$_6$$^-$, B(C$_6$F$_5$)$_4$$^-$, B(C$_6$H$_5$)$_4$$^-$, and CF$_3$SO$_3$$^-$, PF$_6$$^-$;
an organometallic catalyst selected from the group consisting of:
   the iridium complexes of formula (III)

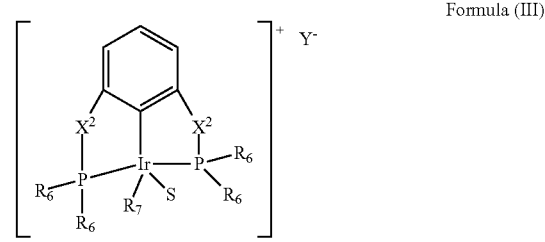

Formula (III)

in which
   R$^6$ represents an alkyl or aryl group;
   R$^7$ represents a hydrogen atom or an alkyl group;
   X$^2$ represents a —CH$_2$— group or an oxygen atom; and
   Y represents a counterion selected from the group consisting of B(C$_6$F$_5$)$_4$ and B(C$_6$H$_5$)$_4$;
   S represents a molecule of solvent, coordinated to the complex, selected from the group consisting of dimethylsulfoxide (DMSO), acetonitrile (CH$_3$CN), and acetone (CH$_3$COCH$_3$); and the ruthenium complexes of formula (V)

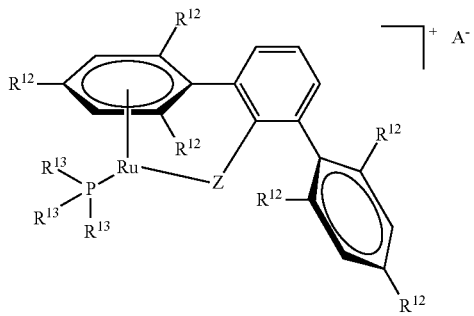

Formula (V)

in which
R$^{12}$ represents a hydrogen atom or an alkyl group;
R$^{13}$ represents an aryl or an alkyl group, said aryl and alkyl groups optionally being substituted;
Z represents a —CH$_2$— group, an oxygen atom or a sulfur atom; and
A$^-$ represents a counterion selected from the group consisting of B(C$_6$F$_5$)$_4$$^-$ and [CHB$_{11}$H$_5$Cl$_6$]$^-$; or
a Lewis acid type catalyst selected from the group consisting of:
    boron compounds selected from the group consisting of BF$_3$, BF$_3$(Et$_2$O), BCl$_3$, BBr$_3$, triphenyl hydroborane, tricyclohexyl hydroborane, B(C$_6$F$_5$)$_3$, B-methoxy-9-borabicyclo[3.3.1]nonane (B-methoxy-9-BBN), and B-benzyl-9-borabicyclo[3.3.1]nonane (B-benzyl-9-BBN);
    borenium compounds Me-TBD-BBN$^+$, the borenium ferrocene derivatives corresponding to formula

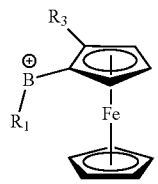

borenium ferrocene in which R$^1$ is a phenyl group and R$^3$ is 3,5-dimethylpyridyl;
    aluminum compounds selected from the group consisting of AlCl$_3$, AlBr$_3$, aluminum isopropoxide Al(O-i-Pr)$_3$, aluminum ethanoate (Al(C$_2$H$_3$O$_2$)), Krossing's salt [Ag(CH$_2$Cl$_2$)]{Al[OC(CF$_3$)$_3$]$_4$}, Li{Al[OC(CF$_3$)$_3$]$_4$}, and Et$_2$Al$^+$;
    indium compounds selected from the group consisting of InCl$_3$ and In(OTf)$_3$;
    iron compounds selected from the group consisting of FeCl$_3$ and Fe(OTf)$_3$;
    tin compounds selected from the group consisting of SnCl$_4$ and Sn(OTf)$_2$;
    phosphorus compounds;
trifluoromethanesulfonate or triflate compounds (CF$_3$SO$_3$$^-$) of transition metals and lanthanides selected from the group consisting of scandium triflate, ytterbium triflate, yttrium triflate, cerium triflate, samarium triflate, and neodymium triflate.

2. The method as claimed in claim 1, wherein the level of sulfur in the lignin is greater than or equal to zero and remains below 1.5 wt %, relative to the total weight of the lignin, as defined below:

0<level of sulfur in the lignin<1.5 wt %, relative to the total weight of lignin.

3. The method as claimed in claim 1, wherein the lignin is extracted from a plant species selected so as to have:
    at least 10 wt % of lignin relative to the total weight of the sample of the plant species selected;
    at least 30% of cleavable bonds relative to the total number of bonds present between the monomer units in the lignin; and
    at least 50% of residue G, H or S of the total number of residues present in the lignin used.

4. The method as claimed in claim 1, wherein the aromatic molecules containing 1 or 2 aromatic rings have an average molar mass by weight less than or equal to 400 g/mol.

5. The method as claimed in claim 1, wherein the silane compound of formula (I), R$^1$, R$^2$, and R$^3$ represent, independently of one another, a hydrogen atom; an alkyl group selected from the group consisting of methyl, ethyl, propyl, butyl, pentyl, hexyl, heptyl groups and their branched isomers; an alkoxy group whose alkyl group is selected from the group consisting of methyl, ethyl, propyl, butyl, pentyl, hexyl, heptyl groups and their branched isomers; an aryl group selected from the group consisting of benzyl and phenyl groups; a silylated group selected from the group consisting of polydimethylsiloxane (PDMS), polymethylhydroxysiloxane (PMHS), and tetramethyldisiloxane (TMDS).

6. The method as claimed in claim 1, wherein the organometallic catalyst is selected from the group consisting of:
    the iridium complex [(POCOP)Ir(H)(acetone)]$^+$B(C$_6$F$_5$)$_4$$^-$ with (POCOP) representing 2,6-bis(di-tert-butylphosphinito)phenyl; and
    the ruthenium complex of formula (V) in which
        R$^{12}$ represents a methyl group;
        R$^{13}$ represents p-FC$_6$H$_4$;
        Z represents a sulfur atom; and
        A$^-$ represents B(C$_6$F$_5$)$_4$$^-$.

7. The method as claimed in claim 1, wherein the catalyst is selected from the group consisting of BF$_3$; InCl$_3$; and triphenylcarbenium tetrakis(perfluorophenyl)borate [(Ph)$_3$C$^+$B(C$_6$F$_5$)$_4$$^-$, B(C$_6$F$_5$)$_3$].

8. The method as claimed in claim 1, wherein the reaction is carried out under a pressure of an inert gas or a mixture of inert gases selected from the group consisting of nitrogen and argon, or gases generated by the process, notably methane and hydrogen, said pressure being between 0.2 and 50 bar, inclusive.

9. The method as claimed in claim 1, wherein the reaction is carried out at a temperature between 0 and 150° C., inclusive.

10. The method as claimed in claim 1, wherein the reaction is carried out in a solvent or a mixture of at least two solvents selected from the group consisting of:
    silylated ethers selected from the group consisting of 1,1,1,3,3,3-hexamethyldisiloxane ((Me$_3$Si)$_2$O) and 1,1,1,3,3,3-hexaethyldisiloxane ((Et$_3$Si)$_2$O);
    hydrocarbons selected from the group consisting of benzene, toluene, pentane, and hexane;
    sulfoxides selected from the group consisting of dimethylsulfoxide (DMSO);
    alkyl halides selected from the group consisting of chloroform, methylene chloride, chlorobenzene, and dichlorobenzene.

11. The method as claimed in claim 1, wherein the weight ratio of the silane compound of formula (I) to the lignin is between 0.5 and 6, inclusive.

12. The method as claimed in claim 1, wherein the amount of catalyst is from 0.001 to 1 equivalent by weight, inclusive, relative to the initial weight of lignin.

13. A method of manufacturing fuels, electronic components, plastics, rubber, medicinal products, vitamins, cosmetics, perfumes, food products, synthetic yarn and fibers, synthetic leather, adhesives, pesticides, fertilizers, or combinations thereof, wherein the method comprises a step of depolymerisation of lignin by the method of claim 1, and thereafter a manufacturing step.

* * * * *